United States Patent
Tokimizu et al.

(10) Patent No.: US 11,850,346 B2
(45) Date of Patent: Dec. 26, 2023

(54) BEADS FOR BLOOD PROCESSING

(71) Applicant: Asahi Kasei Medical Co., Ltd., Tokyo (JP)

(72) Inventors: Yusuke Tokimizu, Tokyo (JP); Satoru Inoue, Tokyo (JP); Yoshihiro Hatanaka, Tokyo (JP)

(73) Assignee: ASAHI KASEI MEDICAL CO., LTD., Tokyo (JP)

( * ) Notice: Subject to any disclaimer, the term of this patent is extended or adjusted under 35 U.S.C. 154(b) by 555 days.

(21) Appl. No.: 17/256,824

(22) PCT Filed: Jun. 27, 2019

(86) PCT No.: PCT/JP2019/025744
§ 371 (c)(1),
(2) Date: Dec. 29, 2020

(87) PCT Pub. No.: WO2020/009008
PCT Pub. Date: Jan. 9, 2020

(65) Prior Publication Data
US 2021/0170362 A1     Jun. 10, 2021

(30) Foreign Application Priority Data

Jul. 2, 2018 (JP) ................. 2018-126227
Jun. 17, 2019 (JP) ................. 2019-112280
Jun. 17, 2019 (JP) ................. 2019-112290

(51) Int. Cl.
*A61M 1/36* (2006.01)
*B01J 20/26* (2006.01)
*B01J 20/28* (2006.01)

(52) U.S. Cl.
CPC .......... *A61M 1/3679* (2013.01); *B01J 20/261* (2013.01); *B01J 20/262* (2013.01);
(Continued)

(58) Field of Classification Search
CPC .............. A61M 1/3486; A61M 1/3621; A61M 1/3679; A61M 1/3687; B01J 20/261;
(Continued)

(56) References Cited

U.S. PATENT DOCUMENTS

2002/0000403 A1   1/2002  Tanaka et al.
2002/0146413 A1  10/2002  Brady et al.
(Continued)

FOREIGN PATENT DOCUMENTS

CN   106905555 A   6/2017
CN   107126936 A   9/2017
(Continued)

OTHER PUBLICATIONS

Extended European Search Report, EPO, Application No. 20217448.8, dated Apr. 29, 2021.
(Continued)

*Primary Examiner* — Brian A McCaig
(74) *Attorney, Agent, or Firm* — GREENBLUM & BERNSTEIN, P.L.C.

(57) ABSTRACT

Provided are beads for blood processing having porous beads and a polymer carried on the surface of the porous beads, wherein: the porous beads are configured from at least one resin selected from the group consisting of acrylic resins, styrene resins, and cellulose resins; and the polymer includes a specific monomer defined in the description as a monomer unit.

17 Claims, 4 Drawing Sheets

(52) U.S. Cl.
CPC ... *B01J 20/28004* (2013.01); *B01J 20/28016* (2013.01); *B01J 20/28071* (2013.01); *B01J 20/28073* (2013.01); *B01J 20/28076* (2013.01); *B01J 2220/445* (2013.01)

(58) Field of Classification Search
CPC .. B01J 20/262; B01J 20/264; B01J 20/28004; B01J 20/28016; B01J 20/28019; B01J 20/28054; B01J 20/28069; B01J 20/28071; B01J 20/28073; B01J 20/28076; B01J 20/28092; B01J 20/321; B01J 20/3212; B01J 20/3244; B01J 20/327; B01J 20/3276; B01J 20/3285; B01J 20/3293; B01J 2220/445
See application file for complete search history.

(56) References Cited

U.S. PATENT DOCUMENTS

| | | |
|---|---|---|
| 2002/0159995 A1 | 10/2002 | Brady et al. |
| 2007/0093739 A1 | 4/2007 | Brady et al. |
| 2010/0300971 A1 | 12/2010 | Jiang et al. |
| 2011/0070424 A1 | 3/2011 | Young et al. |
| 2011/0274594 A1 | 11/2011 | Kitaguchi et al. |
| 2012/0238441 A1 | 9/2012 | Young et al. |
| 2016/0129176 A1 | 5/2016 | Kanaki et al. |
| 2016/0263294 A1 | 9/2016 | Anzai |
| 2016/0303296 A1 | 10/2016 | Anzai |
| 2017/0128636 A1 | 5/2017 | Anzai et al. |
| 2017/0216504 A1 | 8/2017 | Miyamoto et al. |
| 2018/0326136 A1 | 11/2018 | Morita et al. |
| 2020/0246532 A1 | 8/2020 | Golobish et al. |

FOREIGN PATENT DOCUMENTS

| | | | |
|---|---|---|---|
| EP | 2985046 A1 | 2/2016 | |
| JP | H01-119264 A | 5/1989 | |
| JP | 2005-514127 A | 5/2005 | |
| JP | 2007-130194 A | 5/2007 | |
| JP | 2016-514568 A | 5/2016 | |
| JP | 2017-025285 A | 2/2017 | |
| JP | 2017-086563 A | 5/2017 | |
| JP | 2017-185037 A | 10/2017 | |
| WO | 1999/006098 A1 | 2/1999 | |
| WO | 2003/090924 A1 | 11/2003 | |
| WO | 2005/058453 A1 | 6/2005 | |
| WO | 2014/196651 A1 | 12/2014 | |
| WO | 2015/098763 A | 7/2015 | |
| WO | 2015/125890 A | 8/2015 | |
| WO | 2016/052618 A1 | 4/2016 | |
| WO | WO-2017070415 A1 * | 4/2017 | ........... A61K 31/795 |
| WO | 2017/082423 A1 | 5/2017 | |
| WO | 2017/205166 A1 | 11/2017 | |

OTHER PUBLICATIONS

Supplementary European Search Report issued in EPO Patent Application No. 19829748.3, Jul. 27, 2021.
ISR, WIPO Application No. PCT/JP2019/025744, issued Aug. 27, 2019, English translation.
Written Opinion, WIPO, Application No. PCT/JP2019/025744, dated Aug. 27, 2019, English translation.
IPRP, WIPO Application No. PCT/JP2019/025744, issued Jan. 5, 2021, English translation.

* cited by examiner

BEADS FOR BLOOD PROCESSING

FIELD

The present invention relates to beads for blood processing.

BACKGROUND

Treatment of ischemic disease such as sepsis includes various kinds of apheresis therapies that remove potential causative inflammatory mediators of the condition, such as cytokines and alarmins, from patient blood. One type of apheresis therapy has progressed in recent years with the development of adsorption-type blood purification devices that adsorb and remove inflammatory mediators.

Examples of commercially available adsorption-type blood purification devices include TORAYMYXIN™ (Toray Medical Co., Ltd.) which uses an adsorbent comprising fibers with an endotoxin-removing function, wrapped into a roll; sepXiris™ (Baxter International) which is an adsorption-type blood purification device for continuous blood purification therapy (CRRT), using hollow fibers with an alarmin (HMGB1)- and cytokine (such as IL-6)-adsorption function; and CytoSorb™ (Cytosorbents Corp.) which uses porous polymer beads with a cytokine-removing function.

Blood purification devices must be biocompatible since they directly contact with patient blood. To provide blood purification devices with biocompatibility, the adsorbents are coated with biocompatible polymers, and typically hydrophilic polymers.

PTL 1, for example, describes an antithrombotic coating material produced by polymerization reaction after addition of a specific radical polymerization initiator to a methanol solution containing a monomer with a specific structure. The antithrombotic coating material can be coated onto medical equipment such as ePTFE artificial blood vessels and other artificial organs, or catheters, to provide them with biocompatibility.

PTL 2 describes a copolymer having a specific structure comprising a monomer unit with a nonionic group, a monomer unit with a basic nitrogen-containing functional group and a monomer unit with a homopolymerized N value of 2 or lower. When the copolymer is supported on a filter, it is possible to provide a biological fluid-treating filter that is capable of treating biological fluids that contain erythrocytes, without adversely affecting the erythrocytes.

PTL 3 describes coating porous beads with a crosslinked polymer material having one or more of either or both a zwitterionic portion and an oligoethylene glycol portion, for use as an adsorbent.

PTL 4 describes a biocompatible polymer obtained by copolymerization of N-methacryloyloxyethyl-N,N-dimethylammonium-α-N-methylcarboxybetaine (CMB) and a biocompatible polymerizable monomer, represented by an alkene compound having one double bond and an organic group.

PTL 5 describes a biocompatible polymer obtained by copolymerization of 2-methoxyethyl acrylate (MEA) and N-methacryloyloxyethyl-N,N-dimethylammonium-α-N-methylcarboxybetaine (CMB), wherein CMB constitutes 1 to 7 mol % of the total monomer units.

PTL 6 describes a biocompatible polymer obtained by copolymerization of 2-methoxyethyl acrylate (MEA) with [2-(methacryloyloxy)ethyl]dimethyl-(3-sulfopropyl)ammonium hydroxide (SPB) or [3-(methacryloylamino)propyl] dimethyl(3-sulfopropyl)ammonium hydroxide (SPBA), wherein SBAC constitutes 1 to 7 mol % of the total monomer units.

Such adsorption-type blood purification devices are expected to have application not only for treatment of ischemic disease but also for other situations in which excess production of inflammatory mediators is problematic, such as heart surgery and organ transplantation surgery.

CITATION LIST

Patent Literature

[PTL 1] Japanese Unexamined Patent Publication No. 2017-025285
[PTL 2] Japanese Unexamined Patent Publication No. 2017-185037
[PTL 3] Japanese Patent Public Inspection No. 2016-514568
[PTL 4] Japanese Patent Public Inspection No. 2007-130194
[PTL 5] International Patent Publication No. WO2015/098763
[PTL 6] International Patent Publication No. WO2015/125890

SUMMARY

Technical Problem

It is an object of the present invention to solve one or more problems associated with the conventional medical equipment comprising biocompatible polymers described in PTLs 1 to 6.

Namely, when the conventional biocompatible polymers described in PTLs 1 to 3 are coated (or "supported") on porous beads as the adsorbent, the improved biocompatibility of the porous beads is also accompanied by hydrophilicizing of the porous bead surfaces, and consequently reduced adsorption of inflammatory mediators which are hydrophobic proteins. A trade-off situation therefore exists between improvement in biocompatibility and increased adsorption.

In light of this situation, according to a first embodiment it is an object of the invention to provide beads for blood processing that maintain adsorption onto the porous beads while also exhibiting improved blood compatibility.

When the conventional biocompatible polymers described in PTLs 2 to 4 are coated (or "supported") on a medical material, the improved biocompatibility of the medical material is also accompanied by high water solubility of the zwitterion-containing polymers, which results in elution of such polymers into blood when they contact with water or blood. Lower amounts of eluted substances are preferred for an adsorption-type blood purification device, and it is therefore considered necessary for coating polymers to have adequately reduced contents of zwitterion-containing monomer units, as in PTLs 5 and 6.

According to a second embodiment, therefore, it is an object of the invention to provide beads for blood processing with high biocompatibility and low elution of supported biocompatible polymers into blood.

Solution to Problem

As a result of much diligent research conducted with the purpose of solving the problem mentioned above, the present inventors have completed this invention upon finding that, according to the first embodiment, it is possible to solve the problem by supporting, on specified porous beads, a polymer containing a monomer represented by following formula (1) as a monomer unit. Examples of the first embodiment of the invention are as follows.

[1]

Beads for blood processing comprising porous beads and a polymer supported on the surfaces of the porous beads, wherein:
the porous beads are composed of at least one resin selected from the group consisting of acrylic-based resins, styrene-based resins and cellulose-based resins, and
the polymer includes, as a monomer unit, a monomer represented by following formula (1):

[Chemical Formula 1]

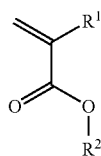

(1)

where $R^1$ is $-CH_3$, $R^2$ is $-CH_2(CH_2)_qOCH_3$ or $-CH_2C_mH_{2m+1}$, q is 1 to 5 and m is 0 to 17.

[2]

The beads for blood processing according to [1], wherein the proportion of nitrogen atoms on the surfaces of the beads for blood processing is 0.2% to 0.7%, as the percentage of atoms based on the total number of atoms with atomic numbers of 3 to 92.

[3]

The porous adsorbing beads according to [1] or [2], wherein q is 1 or 2 and m is 0 to 11.

[4]

The beads for blood processing according to any one of [1] to [3], wherein the content of the monomer represented by formula (1) is 40 mol % or greater with respect to the total monomers composing the polymer.

[5]

The beads for blood processing according to any one of [1] to [4], wherein the polymer further includes a charged monomer as a monomer unit.

[6]

The beads for blood processing according to [5], wherein the charged monomer is a monomer with at least one group selected from the group consisting of amino, carboxyl, phosphate, sulfonate and zwitterionic groups.

[7]

The beads for blood processing according to [5], wherein the charged monomer is at least one selected from the group consisting of 2-aminoethyl methacrylate (AEMA), dimethylaminoethyl methacrylate (DMAEMA), diethylaminoethyl methacrylate (DEAEMA), [2-(methacryloyloxy)ethyl]trimethylammonium, acrylic acid (AAc), methacrylic acid (MAc), N-methacryloyloxyethyl-N,N-dimethylammonium-α-N-methylcarboxybetaine (CMB) and 2-(methacryloyloxy)ethyl 2-(trimethylammonio)ethyl phosphate (MPC).

[8]

The beads for blood processing according to any one of [5] to [7], wherein the content of the charged monomer is 10 mol % to 60 mol % with respect to the total monomers composing the polymer.

[9]

The beads for blood processing according to any one of [5] to [7], wherein the content of the charged monomer is 15 mol % to 40 mol % with respect to the total monomers composing the polymer.

[10]

The beads for blood processing according to any one of [1] to [9], wherein the proportion of the sum of carbon atoms and oxygen atoms on the surfaces of the beads for blood processing is 97.0% or higher, as the percentage of atoms based on the total number of atoms with atomic numbers of 3 to 92.

[11]

The beads for blood processing according to any one of [1] to [10], wherein the amount of the polymer is 0.08 mg to 114 mg per 1 g of dry weight of the porous beads.

[12]

The beads for blood processing according to any one of [1] to [10], wherein the amount of the polymer is 2.0 mg to 20 mg per 1 g of dry weight of the porous beads.

[13]

The beads for blood processing according to any one of [1] to [12], wherein the porous beads have a volume-average particle size of 300 μm to 1000 μm.

[14]

The beads for blood processing according to any one of [1] to [13], wherein the porous beads have a cumulative pore capacity for pore sizes of 5 nm to 100 nm of 0.5 cm$^3$/g or higher and a cumulative pore capacity for pore sizes of 100 nm to 1000 nm of 0.2 cm$^3$/g or lower.

[15]

The beads for blood processing according to any one of [1] to [14], wherein the monomer represented by formula (1) is at least one selected from the group consisting of 2-methoxyethyl methacrylate, n-butyl methacrylate and lauryl methacrylate.

[16]

The beads for blood processing according to any one of [1] to [15], which remove hydrophobic protein molecules of greater than 1000 Da to less than 66,000 Da from blood.

[17]

The porous adsorbing beads according to any one of [1] to [16], which remove cytokines and high-mobility group box 1 (HMGB1) from blood.

[18]

A blood purification device comprising the beads for blood processing according to any one of [1] to [17].

As a result of much diligent research directed toward solving the problems mentioned above, the present inventors have also completed this invention upon finding that, according to a second embodiment, if a polymer comprising a specific amount of a zwitterionic monomer as a monomer unit is supported in a specific amount on the surfaces of porous beads composed of a specific resin, as a medical material, it is possible to inhibit the amount of elution of the polymer into water. Examples of the second embodiment of the invention are as follows.

[19]

Beads for blood processing comprising porous beads and a polymer supported on the surfaces of the porous beads, wherein:
the porous beads are composed of at least one resin selected from the group consisting of acrylic-based resins, styrene-based resins and cellulose-based resins,
the polymer includes a zwitterionic monomer as a monomer unit, and the zwitterionic monomer content is 10 mol % to 30 mol % based on the total monomers composing the polymer.

[20]

The beads for blood processing according to [19], wherein the proportion of nitrogen atoms on the surfaces of the beads for blood processing is 0.2% to 0.9%, as the percentage of atoms based on the total number of atoms with atomic numbers of 3 to 92.

[21]

The beads for blood processing according to [19] or [20], wherein:

the zwitterionic monomer is at least one selected from the group consisting of monomers represented by following formula (2):

[Chemical Formula 2]

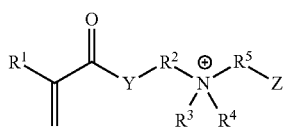

(2)

where $R^1$ is a hydrogen atom or a methyl group, Y is an oxygen atom or —NH—, $R^2$ is —$CH_2(CH_2)_q$—, q is 1 to 5, $R^3$ and $R^4$ are each independently a hydrogen atom or an alkyl group of 1 to 4 carbon atoms, $R^5$ is —$CH_2(CH_2)_m$—, m is 0 to 4 and Z is —$COO^-$ or $SO_3^-$, and monomers represented by following formula (3):

[Chemical Formula 3]

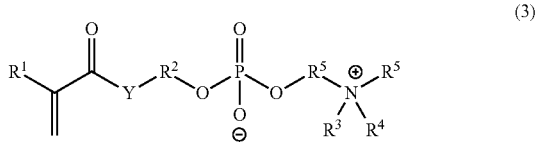

(3)

where $R^1$ is a hydrogen atom or a methyl group, Y is an oxygen atom or —NH—, $R^2$ is —$CH_2(CH_2)_q$—, q is 1 to 5, $R^3$, $R^4$ and $R^6$ are each independently a hydrogen atom or an alkyl group of 1 to 4 carbon atoms, $R^5$ is —$CH_2(CH_2)_m$— and m is 0 to 4.

[22]

The beads for blood processing according to any one of [19] to [21], wherein the polymer further includes, as a monomer unit, a monomer represented by following formula (4):

[Chemical Formula 4]

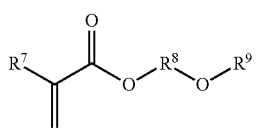

(4)

where $R^7$ is a hydrogen atom or a methyl group, $R^8$ is —$CH_2(CH_2)_r$—, r is 1 to 5, $R^9$ is —$CH_2C_tH_{2t+1}$ and t is 0 to 3.

[23]

The beads for blood processing according to [22], wherein the polymer is composed of the zwitterionic monomer and the monomer of formula (4).

[24]

The beads for blood processing according to any one of [19] to [23], wherein in formula (4), r is 1 to 3 and t is 0 or 1.

[25]

The beads for blood processing according to any one of [19] to [24], wherein in formula (2), $R^1$ is a methyl group, q is 1 to 3, $R^3$ and $R^4$ are each independently a methyl or ethyl group and m is 0 or 1.

[26]

The beads for blood processing according to any one of [19] to [25], wherein the zwitterionic monomer is at least one selected from the group consisting of N-methacryloyloxyethyl-N,N-dimethylammonium-α-N-methylcarboxybetaine, [2-(methacryloyloxy)ethyl]dimethyl-(3-sulfopropyl)ammonium hydroxide, [3-(methacryloylamino)propyl]dimethyl(3-sulfopropyl)ammonium hydroxide and 2-(methacryloyloxy)ethyl 2-(trimethylammonio)ethyl phosphate.

[27]

The beads for blood processing according to any one of [19] to [16], wherein the porous beads have a cumulative pore capacity for pore sizes of 5 nm to 100 nm of 0.5 $cm^3/g$ or higher and a cumulative pore capacity for pore sizes of 100 nm to 200 nm of 0.2 $cm^3/g$ or lower.

[28]

The beads for blood processing according to any one of [19] to [27], wherein the porous beads have a volume-average particle size of 300 μm to 1000 μm.

[29]

The beads for blood processing according to any one of [19] to [18], which remove hydrophobic protein molecules of greater than 1000 Da to less than 66,000 Da from blood.

[30]

The porous adsorbing beads according to any one of [19] to [29], which remove cytokines and high-mobility group box 1 (HMGB1) from blood.

[31]

A blood purification device comprising the beads for blood processing according to any one of [19] to [30].

Advantageous Effects of Invention

According to the invention it is possible to solve one or more problems of medical equipment comprising biocompatible polymers of the prior art. The preceding description should not be construed as disclosing all of the embodiments of the invention nor all of the advantages of the invention. Additional embodiments or advantages of the invention will become apparent with reference to the following description and drawings.

DESCRIPTION OF EMBODIMENTS

Figure 1:
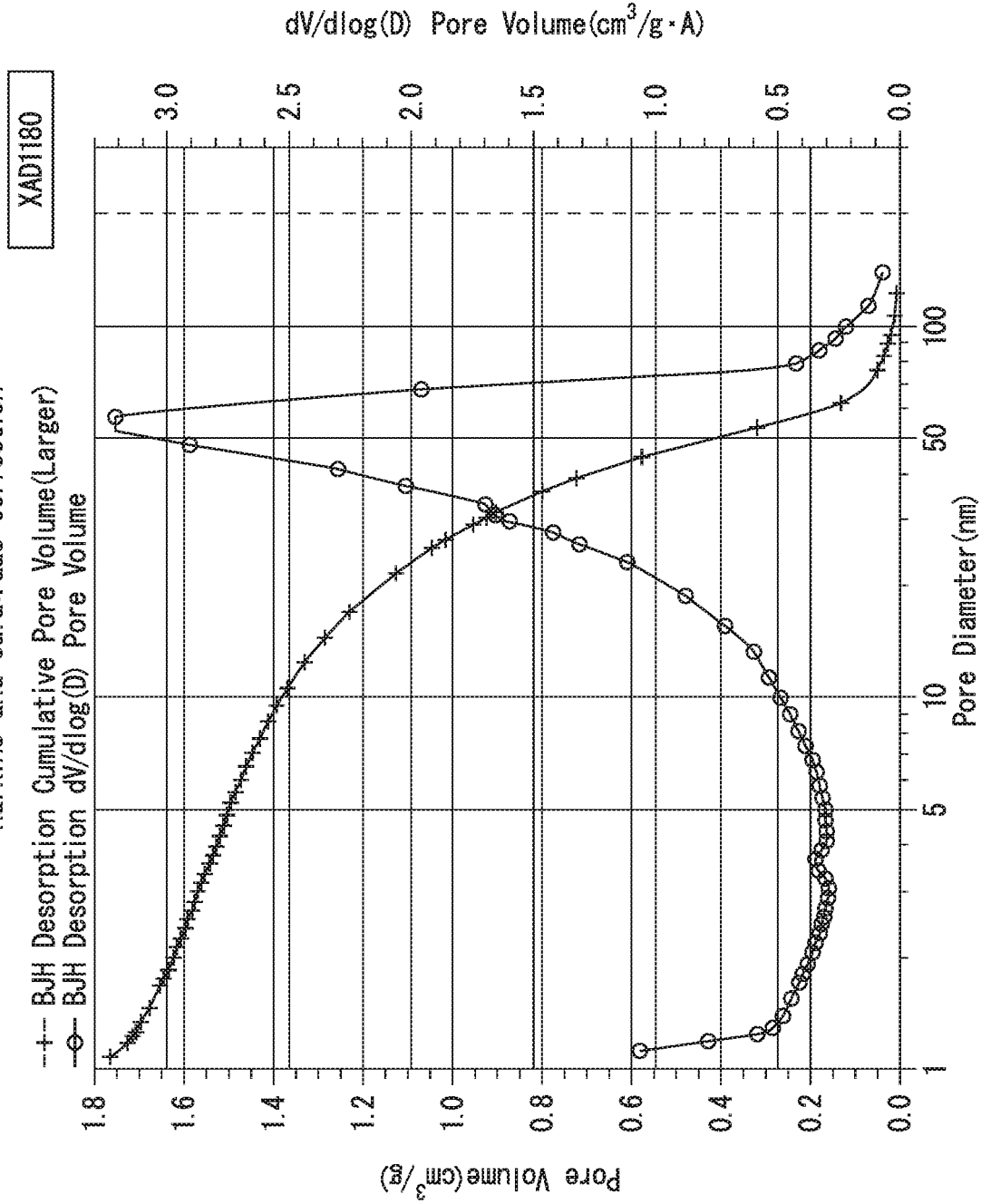
FIG. 1 is a graph showing log differential pore volume distribution and cumulative pore capacity, for AMBERLITE™ XAD™ 1180N (styrene-based polymer beads by Organo Co., Ltd.).

First and second embodiments of the invention (hereunder also collectively referred to as "embodiments") will now be explained in detail as examples, with the understanding that the invention is not limited to the embodiments. The upper limits and lower limits for the numerical ranges throughout the present specification may be combined as desired.

<Beads for Blood Processing>
<Biocompatible Polymer>

The beads for blood processing of the first embodiment comprise a polymer supported on porous beads as an adsorbent. The polymer is a polymer that includes a monomer represented by the following formula (1) as a monomer unit (hereunder also referred to as "biocompatible polymer").

[Chemical Formula 5]

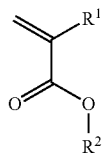

(1)

In formula (1), $R^1$ is a methyl group (—$CH_3$). $R^2$ is a straight-chain alkyl group with a methoxy group at the end (—$CH_2(CH_2)_q OCH_3$), or an alkyl group (—$CH_2 C_m H_{2m+1}$). In $R^2$, q is 1 to 5, preferably 1 to 3 and more preferably 1 or 2, and m is 0 to 17 and preferably 0 to 11. When $R^2$ is an alkyl group (—$CH_2 C_m H_{2m+1}$), the $C_m H_{2m+1}$ portion may be a straight chain or branched chain, but it is preferably a straight chain.

The monomer represented by formula (1) is preferably one or more selected from the group consisting of 2-methoxyethyl methacrylate (MEMA), n-butyl methacrylate (BMA), and lauryl methacrylate (LMA), and even more preferably 2-methoxyethyl methacrylate (MEMA). The monomer represented by formula (1) is preferably one of those mentioned above, since this will allow higher excess adsorption to be maintained on the porous beads, and can improve blood compatibility.

Without being limited to any particular theory, the beads for blood processing of the first embodiment, having a biocompatible polymer that includes as a monomer unit a monomer in which $R^1$ is a methyl group (—$CH_3$) and $R^2$ is a specific group, supported on porous beads composed of a specific material, can maintain adsorption of the porous beads while increasing the blood compatibility. Although the mechanism is still not completely understood at the time of the present filing, the present inventors conjecture as follows. When porous beads have been treated with a biocompatible polymer in the prior art, it has been considered preferable to impregnate the porous beads with more biocompatible polymer in order to ensure sufficient biocompatibility. Therefore, biocompatible polymers with high impregnating properties for porous beads have been preferred for use. The pores in the porous bead interiors (adsorption sites) thus become excessively hydrophilicized by the hydrophilicity of the biocompatible polymer, impeding adsorption of hydrophobic inflammatory mediators. Presumably, when the adsorption sites inside the porous beads become physically blocked by the biocompatible polymer, the adsorption property is reduced. Thus, improvement in the biocompatibility of porous beads and increase in adsorption have conventionally been in a trade-off relationship.

However, by combining the aforementioned specific biocompatible polymer and porous beads composed of a specific material, the beads for blood processing of the first embodiment improves the hydrophilic/hydrophobic balance on the surfaces and adsorption sites of the porous beads. In addition, according to another embodiment, the impregnating property for the porous beads is adjusted as appropriate by changing the combination of the aforementioned specific biocompatible polymer and porous beads composed of a specific material. The reason is that a biocompatible polymer in which $R^1$ is a hydrogen atom tends to have a high impregnating property in porous beads, and coats the entirety of the surfaces of the porous beads composed of the material described herein in a non-selective manner, i.e. uniformly. On the other hand, a polymer according to the first embodiment, which includes as a monomer unit a monomer wherein $R^1$ is a methyl group, has a suitably limited impregnating property for porous beads, and for different porous bead surfaces, it tends to coat preferentially onto easily adherable rough surfaces rather than smooth surfaces that are resistant to adhesion of biocompatible polymers. The smooth surfaces of porous beads therefore tend to remain without adhesion of biocompatible polymers. This tendency also applies to platelets, with platelets readily adhering onto rough surfaces rather than the smooth surfaces of beads. Since the polymer of the first embodiment preferentially adheres onto rough surfaces, it is possible to effectively reduce adhesion of platelets onto the bead surfaces. If surfaces are present where the biocompatible polymer is not adhering, then the amount of biocompatible polymer supported on the porous beads will be suppressed while reducing blockage of adsorption sites. The beads for blood processing of the first embodiment can thereby maintain the adsorption property of the porous beads while increasing blood compatibility. Unexpectedly, therefore, the beads for blood processing of the first embodiment are able to provide both biocompatibility and adsorption, as properties which in the past have been considered to be in a trade-off relationship.

The content of the monomer represented by formula (1) is preferably 40 mol % or greater and more preferably 60 mol % or greater, based on the entire amount of monomers composing the biocompatible polymer. The upper limit for the monomer content is not limited, and it may be 100 mol %, or 80 mol % or less or 60 mol % or less, based on the entire amount of monomers composing the biocompatible polymer.

According to the first embodiment, the biocompatible polymer preferably further includes as another monomer unit, a charged monomer that is copolymerizable with the monomer represented by formula (1). As used herein, "charged monomer" is a monomer having a functional group that is partially or completely charged with a positive charge or negative charge under conditions of pH 7.0. When the biocompatible polymer further includes a charged monomer as a monomer unit, then its use in combination with the porous beads of the first embodiment lowers the amount of biocompatible polymer supported on the porous beads and can help prevent reduction in adsorption. The charged monomer also has increased biocompatibility due to its high hydrophilicity. This tends to result in beads for blood processing that have more satisfactory adsorption and blood compatibility.

According to the first embodiment, the charged monomer may be a monomer with at least one group selected from the group consisting of amino groups (—NH$_2$, —NHR$^3$, NR$^3$R$^4$), carboxyl groups (—COOH), phosphate groups (—OPO$_3$H$_2$), sulfonate groups (—SO$_3$H) and zwitterionic groups. For amino groups, preferably R$^3$ and R$^4$ are each independently an alkyl group of 1 to 3 carbon atoms, and more preferably an alkyl group of 1 or 2 carbon atoms.

Among these, the charged monomer is more preferably a monomer having at least one group selected from the group consisting of amino, carboxyl and zwitterionic groups. The charged monomer even more preferably is at least one selected from the group consisting of cationic monomers with amino groups, anionic monomers with carboxyl groups, zwitterionic monomers with amino groups and carboxyl groups, and zwitterionic monomers with amino groups and phosphate groups. The charged monomer even more preferably has a carboxyl group from the viewpoint of adsorption of Ca$^{2+}$ by the porous beads, and inhibiting acceleration of blood clotting.

More specifically, the charged monomer is more preferably at least one selected from the group consisting of 2-aminoethyl methacrylate (AEMA), dimethylaminoethyl methacrylate (DMAEMA), diethylaminoethyl methacrylate (DEAEMA), [2-(methacryloyloxy)ethyl]trimethylammonium, acrylic acid (AAc), methacrylic acid (MAc), 2-(methacryloyloxy)ethyl phosphate, N-methacryloyloxyethyl-N,N-dimethylammonium-α-N-methylcarboxybetaine (CMB), [2-(methacryloyloxy)ethyl]dimethyl-(3-sulfopropyl)ammonium hydroxide (SPB), [3-(methacryloylamino)propyl]dimethyl(3-sulfopropyl)ammonium hydroxide (SPBA), 2-(methacryloyloxy)ethyl 2-(trimethylammonio)ethyl phosphate (MPC) and [3-(methacryloylamino)propyl]dimethyl(3-sulfobutyl)ammonium.

Among these, the charged monomer is more preferably at least one selected from the group consisting of methylaminoethyl methacrylate (DMAEMA), diethylaminoethyl methacrylate (DEAEMA), acrylic acid (AAc), N-methacryloyloxyethyl-N,N-dimethylammonium-α-N-methylcarboxybetaine (CMB) and 2-(methacryloyloxy)ethyl 2-(trimethylammonio)ethyl phosphate (MPC), and even more preferably N-methacryloyloxyethyl-N,N-dimethylammonium-α-N-methylcarboxybetaine (CMB).

The charged monomer content for the first embodiment is preferably 10 mol % to 60 mol % and more preferably 15 mol % to 40 mol %, based on the total monomers composing the biocompatible polymer. If the charged monomer content is within this range, the balance between the impregnating property and hydrophilicity of the porous beads will tend to be excellent, and beads for blood processing with superior adsorption and biocompatibility will tend to be obtained. Methods of analyzing the composition and structure of biocompatible polymers will be described in detail below under "Examples".

According to the first embodiment, the weight-average molecular weight (Mw) of the biocompatible polymer is preferably 5,000 to 5,000,000, more preferably 10,000 to 1,000,000 and even more preferably 10,000 to 300,000. The weight-average molecular weight of the biocompatible polymer is preferably within this range from the viewpoint of suitable impregnation into the porous beads, preventing elution into blood, and lowering the supported amount. The method of analyzing the weight-average molecular weight (Mw) of the biocompatible polymer may be measurement by gel permeation chromatography (GPC), as described for the Comparative Examples.

According to the first embodiment, the amount of biocompatible polymer supported on the porous beads (supported amount) is preferably 0.08 mg to 114 mg, more preferably 0.8 mg to 56 mg and even more preferably 2.0 mg to 20 mg, with respect to 1 g of dry weight of the porous beads. The method of measuring the supported amount (coating amount) of the biocompatible polymer is described in detail below under "Examples".

The supported amount can be limited to within this range for the first embodiment by appropriate combination of the biocompatible polymer and the porous beads composed of the specific material. According to another embodiment, the conditions for applying the biocompatible polymer to the porous beads may be changed to control the range of the supported amount. If the supported amount is within the specified range, presumably blockage of the adsorption sites is reduced, and consequently higher adsorption of the porous beads is maintained while also allowing the blood compatibility to be increased.

That the biocompatible polymer is "supported on the surfaces of the porous beads" means, in other words, that the biocompatible polymer is present at least on portions of the surfaces of the porous beads. According to the first embodiment, therefore, it is not necessary for the biocompatible polymer to be supported (coated) over the entire surfaces of the porous beads. So long as the object of the invention is achieved, the biocompatible polymer may be present inside the pores of the porous beads, or blocking the pores to some extent.

According to the first embodiment, the biocompatible polymer may further include another monomer, in addition to the monomer of formula (1) and an optional charged monomer, as a monomer unit. The other monomer is not restricted so long as it is copolymerizable with the aforementioned monomers.

According to the first embodiment, examples of other monomers include monomers wherein, in formula (1), R$^1$ is hydrogen (H) or an alkyl group of 2 or more carbon atoms; a monomer in which for —CH$_2$(CH$_2$)$_q$OCH$_3$ as R$^2$, the terminal group is not a methoxy group but an alkoxy group of two or more carbon atoms, such as an ethoxy, propoxy or butoxy group; a monomer in which for —CH$_2$(CH$_2$)$_q$OCH$_3$ as R$^2$, q is 0 or 6 or greater; a monomer in which for —CH$_2$C$_m$H$_{2m+1}$ as R$^2$, m is 18 or greater; or a combination of the foregoing.

For the first embodiment, the other monomer may be, more specifically, methyl acrylate, ethyl acrylate, isopropyl acrylate, butyl acrylate, hexyl acrylate, 2-ethylhexyl acrylate, methyl methacrylate, methoxymethyl acrylate, methoxyethyl acrylate, methoxypropyl acrylate, methoxybutyl acrylate, ethoxymethyl acrylate, ethoxyethyl acrylate, ethoxypropyl acrylate, ethoxybutyl acrylate, propoxymethyl acrylate, propoxyethyl acrylate, propoxypropyl acrylate, propoxybutyl acrylate, butoxymethyl acrylate, butoxyethyl acrylate, butoxypropyl acrylate, butoxybutyl acrylate, ethoxymethyl methacrylate, ethoxyethyl methacrylate, ethoxypropyl methacrylate, ethoxybutyl methacrylate, propoxymethyl methacrylate, propoxyethyl methacrylate, propoxypropyl methacrylate, propoxybutyl methacrylate, butoxymethyl methacrylate, butoxyethyl methacrylate, butoxypropyl methacrylate or butoxybutyl methacrylate.

The beads for blood processing of the second embodiment comprise a polymer supported on porous beads as an adsorbent. The polymer is a polymer that includes a zwitterionic monomer as a monomer unit (also referred to as "biocompatible polymer"). As used herein, "zwitterionic monomer" means a monomer having both a positive charge and negative charge in the same molecule under conditions of pH 7.0. If the biocompatible polymer includes a zwitterionic monomer as a monomer unit and is combined with porous beads composed of the material specified below, then beads for blood processing can be provided with high biocompatibility and low elution of the supported biocompatible polymer into blood. Without being limited to any particular theory, the present inventors believe the reason for this to be as follows. Specifically, biocompatibility can be increased because zwitterionic monomers have high hydrophilicity, but in the past this has also led to the problem of greater elution when contacted with water or blood. With adsorption-type blood purification devices, in particular, beads for blood processing are in continuous contact with blood for periods of from several hours to more than a day in some cases. When the coated polymer on the porous beads elutes during use, it becomes impossible to maintain the biocompatibility of the adsorption-type blood purification device for long periods, and the potential for elution of the polymer into the blood increases even further. According to the second embodiment, the porous beads supporting the polymer function as adsorbents, allowing the eluting biocompatible polymer to be adsorbed inside the pores. As a result, it is possible to obtain beads for blood processing with more satisfactory blood compatibility and reduced elution of the biocompatible polymer into blood.

According to the second embodiment, the zwitterionic monomer is preferably at least one selected from the group consisting of zwitterionic monomers with an amino group ($-NH_2$, $-NHR^3$, $NR^3R^4$) and a carboxyl group ($-COOH$), zwitterionic monomers with an amino group and a sulfonate group ($-SO_3H$), and zwitterionic monomers with an amino group and a phosphate group ($-OPO_3H_2$), and more preferably it is a zwitterionic monomer with an amino group and a carboxyl group, from the viewpoint of adsorption of $Ca^{2+}$ by the porous beads and inhibiting acceleration of blood clotting.

According to the second embodiment, the zwitterionic monomer is preferably a monomer represented by following formula (2):

[Chemical Formula 6]

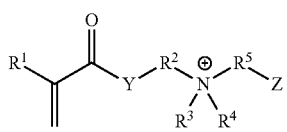

(2)

{where $R^1$ is a hydrogen atom or a methyl group, Y is an oxygen atom or $-NH-$, $R^2$ is $-CH_2(CH_2)_q-$, q is 1 to 5, $R^3$ and $R^4$ are each independently a hydrogen or an alkyl group of 1 to 4 carbon atoms, $R^5$ is $-CH_2(CH_2)_m-$, m is 0 to 4 and Z is $-COO^-$ or $SO_3^-$}.

In formula (2), preferably $R^1$ is a methyl group, q is 1 to 3, $R^3$ and $R^4$ are each independently a methyl or ethyl group, and m is 0 or 1.

The monomer of formula (2) is more preferably at least one selected from the group consisting of N-methacryloyloxyethyl-N,N-dimethylammonium-α-N-methylcarboxybetaine (CMB), [2-(methacryloyloxy)ethyl]dimethyl-(3-sulfopropyl)ammonium hydroxide (SPB), [3-(methacryloylamino)propyl]dimethyl(3-sulfopropyl) ammonium hydroxide (SPBA) and [3-(methacryloylamino)propyl]dimethyl(3-sulfobutyl)ammonium. The monomer of formula (2) is preferably N-methacryloyloxyethyl-N,N-dimethylammonium-α-N-methylcarboxybetaine (CMB) from the viewpoint of adsorption of $Ca^{2+}$ by the porous beads, and inhibiting acceleration of blood clotting.

According to the second embodiment, the zwitterionic monomer is also preferably a monomer represented by following formula (3):

[Chemical Formula 7]

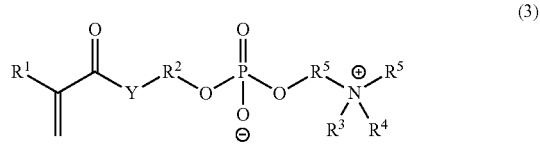

(3)

{where $R^1$ is a hydrogen atom or a methyl group, Y is an oxygen atom or $-NH-$, $R^2$ is $-CH_2(CH_2)_q-$, q is 1 to 5, $R^3$, $R^4$ and $R^6$ are each independently a hydrogen atom or an alkyl group of 1 to 4 carbon atoms, $R^5$ is $-CH_2(CH_2)_m-$ and m is 0 to 4}.

In formula (3), preferably $R^1$ is a methyl group, q is 1 to 3, $R^3$, $R^4$ and $R^6$ are each independently a methyl or ethyl group, and m is 1 or 2.

The monomer of formula (3) may be 2-(methacryloyloxy)ethyl 2-(trimethylammonio)ethyl phosphate (MPC).

For the second embodiment, the zwitterionic monomer is preferably at least one monomer selected from the group consisting of monomers of formulas (2) and (3).

The zwitterionic monomer content for the second embodiment is preferably 10 mol % to 30 mol %, more preferably 12 mol % to 30 mol % and even more preferably 15 mol % to 30 mol %, based on the total monomers composing the biocompatible polymer. If the zwitterionic monomer content is within this range, elution of the biocompatible polymer into water will be inhibited while beads for blood processing with higher biocompatibility will tend to be obtained. Methods of analyzing the composition and structure of biocompatible polymers will be described in detail below under "Examples".

For the second embodiment, the polymer preferably further includes a monomer represented by following formula (4):

[Chemical Formula 8]

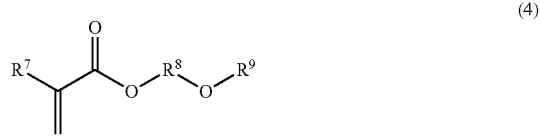

(4)

{where $R^7$ is a hydrogen atom or a methyl group, $R^8$ is $-CH_2(CH_2)_r-$, r is 1 to 5, $R^9$ is $-CH_2C_tH_{2t+1}$ and t is 0 to 3} as a monomer unit, in order to inhibit the amount of elution of the biocompatible polymer into water and obtain beads for blood processing that have higher biocompatibility.

In formula (4), $R^7$ is preferably a methyl group, r is preferably 1 to 3 and more preferably 1 or 2, and t is preferably 0 to 2 and more preferably 0 or 1.

The content of the monomer represented by formula (4) is preferably 40 mol % or greater and more preferably 60 mol % or greater, with respect to the entire amount of monomers composing the biocompatible polymer. The upper limit for the monomer content is not limited, and it is preferably 90 mol % or less, 80 mol % or less or 60 mol % or less, based on the entire amount of monomers composing the biocompatible polymer.

According to the second embodiment, the weight-average molecular weight (Mw) of the biocompatible polymer is preferably 5,000 to 5,000,000, more preferably 10,000 to 1,000,000 and even more preferably 10,000 to 300,000. The weight-average molecular weight of the biocompatible polymer is preferably within this range from the viewpoint of suitable impregnation into the porous beads, preventing elution into blood, and lowering the supported amount. The method of analyzing the weight-average molecular weight (Mw) of the biocompatible polymer may be measurement by gel permeation chromatography (GPC), as described for the Comparative Examples.

That the biocompatible polymer is "supported on the surfaces of the porous beads" means, in other words, that the biocompatible polymer is present at least on portions of the surfaces of the porous beads. According to the second embodiment, therefore, it is not necessary for the biocompatible polymer to be supported (coated) over the entirety of the surfaces of the porous beads. So long as the object of the invention is achieved, the biocompatible polymer may be present inside the pores of the porous beads, or blocking the pores to some extent.

For the second embodiment, the biocompatible polymer may also be composed of the zwitterionic monomer described above and a monomer of formula (4) above. The biocompatible polymer may also include another monomer, however, in addition to the zwitterionic monomer and the monomer of formula (4), as a monomer unit. The other monomer is not restricted so long as it is copolymerizable with the aforementioned monomers.

The other monomer for the second embodiment is a monomer that is not zwitterionic and does not qualify as formula (4). The other monomer may be, for example, a cationic or anionic monomer having a functional group with a partial or complete positive charge under conditions of pH 7.0, or a functional group with a negative charge. Examples of functional groups with positive charges or negative charges include amino groups ($-NH_2$, $-NHR^3$, $NR^3R^4$), carboxyl groups ($-COOH$), phosphate groups ($-OPO_3H_2$) and sulfonate groups ($-SO_3H$). More specifically, cationic and anionic monomers include 2-aminoethyl methacrylate (AEMA), dimethylaminoethyl methacrylate (DMAEMA), diethylaminoethyl methacrylate (DEAEMA), [2-(methacryloyloxy)ethyl]trimethylammonium, acrylic acid (AAc), methacrylic acid (MAc) and 2-(methacryloyloxy)ethyl phosphate. Other monomers include, specifically, methyl acrylate, ethyl acrylate, isopropyl acrylate, butyl acrylate, hexyl acrylate, 2-ethylhexyl acrylate, methyl methacrylate, ethyl methacrylate, isopropyl methacrylate, butyl methacrylate, hexyl methacrylate, 2-ethylhexyl methacrylate, methoxymethyl acrylate, ethoxymethyl acrylate, propoxymethyl acrylate, butoxymethyl acrylate, ethoxymethyl methacrylate, propoxymethyl methacrylate, butoxymethyl methacrylate and 2-(2-ethoxyethoxy)ethyl acrylate (Et2A). Preferred among these are combinations of zwitterionic monomers and monomers of formula (4), with cationic or anionic monomers.

For the second embodiment, the amount of other monomer when present may be 1 mol % or greater, 5 mol % or greater or 10 mol % or greater, and 30 mol % or less, 25 mol % or less or 20 mol % or less, based on the total amount of monomers composing the biocompatible polymer.

<Porous Beads>

The beads for blood processing of this embodiment comprise porous beads as the adsorbent. The porous beads are composed of one or more resins selected from the group consisting of acrylic-based resins, styrene-based resins and cellulose-based resins. For the purpose of the present specification, the porous beads may also contain other resins or components, so long as the object of the invention can be achieved.

The porous beads used may also be commercially available porous beads. Examples of commercially available porous beads composed of acrylic-based resins include AMBERLITE™ XAD™ 7HP (product of Organo Co., Ltd.), DIAION™ HP2MG (product of Mitsubishi Chemical Holdings Corp.), PuroSorb™ PAD610 (product of Purolite Corp.), PuroSorb™ PAD950 (product of Purolite Corp.) and Muromac® PAP-9210 (product of Muromachi Chemicals, Inc.). Examples of commercially available porous beads composed of styrene-based resins include AMBERLITE™ XAD™ 4 (product of Organo Co., Ltd.), AMBERLITE™ XAD™ 2000 (product of Organo Co., Ltd.), AMBERLITE™ FPX66 (product of Organo Co., Ltd.), AMBERLITE™ XAD™ 1180N (product of Organo Co., Ltd.), DIAION™ HP20 (product of Mitsubishi Chemical Holdings Corp.), DIAION™ HP21 (product of Mitsubishi Chemical Holdings Corp.), DIAION™ SP700 (product of Mitsubishi Chemical Holdings Corp.), PuroSorb™ PAD600 (product of Purolite Corp.), PuroSorb™ PAD900 (product of Purolite Corp.) and Muromac® SAP-9210 (product of Muromachi Chemicals, Inc.). Examples of commercially available porous beads composed of cellulose-based resins include VISCOPEARL® MINI (product of Rengo Co., Ltd.) and C8329 (product of Sigma-Aldrich).

The volume-average particle size of the porous beads is preferably 300 μm to 1000 μm, more preferably 400 μm to 800 μm and even more preferably 420 μm to 700 μm. If the volume-average particle size is 300 μm or greater, it is possible to effectively inhibit pressure increase when blood flows through the column, and if the volume-average particle size is 1000 μm or smaller it is possible to exhibit rapid adsorption performance. The method of measuring the "volume-average particle size" of porous beads is described below under "Examples".

The cumulative pore capacity for a porous bead pore size of 5 nm to 100 nm is preferably 0.5 $cm^3/g$ or higher, more preferably 0.8 $cm^3/g$ or higher and even more preferably 1.0 $cm^3/g$ or higher. The upper limit for the cumulative pore capacity is preferably 3.5 $cm^3/g$ or lower, more preferably 3.0 $cm^3/g$ or lower and even more preferably 2.5 $cm^3/g$ or lower. The cumulative pore capacity is preferably within this range since it will allow the adsorption of the porous beads supporting the polymer to be further increased, and will allow the porous beads to remove more hydrophobic protein molecules. A cumulative pore capacity within this range will also allow eluting biocompatible polymer to be more effectively adsorbed inside the pores. The range is therefore preferred in order to make it possible to obtain beads for blood processing with more satisfactory blood compatibility and reduced elution of the biocompatible polymer into blood.

In addition to the feature of the cumulative pore capacity, or according to another embodiment, the cumulative pore capacity with a porous bead pore size of 100 nm to 200 nm is preferably 0.2 $cm^3/g$ or lower, more preferably 0.1 $cm^3/g$ or lower and even more preferably 0.05 $cm^3/g$ or lower. The cumulative pore capacity preferably has this feature since it will allow the porous beads to have more pores of sizes suited for adsorption of hydrophobic protein molecules, resulting in beads for blood processing that have superior adsorption properties. The method of measuring the cumulative pore capacity of the porous beads is described in detail below under "Examples".

<Element Ratio and Atomic Ratio of Beads for Blood Processing>

(Element Ratio Based on Elemental Analysis)

The ratio of nitrogen among the elements composing the beads for blood processing is preferably higher than 0 weight % and 1.0 weight % or lower, and more preferably higher than 0 weight % and 0.3 weight % or lower. The nitrogen element ratio is preferably within this range, since it will allow the beads for blood processing to have high blood compatibility while adsorbing hydrophobic protein molecules. The total of carbon, hydrogen and oxygen among the elements composing the beads for blood processing is preferably higher than 97.0 weight % or higher and more preferably 99.0 weight % or higher. The ratio of these elements is preferably within this range, since it will allow the beads for blood processing to remove more hydrophobic protein molecules. The element ratio based on the elements composing the beads for blood processing can be measured by elemental analysis. The measuring method is described in detail under "Examples".

(Atomic Ratio Based on XPS)

In addition to the feature of the element ratio based on elemental analysis, or according to another embodiment, the ratio of nitrogen atoms on the surfaces of the beads for blood processing is preferably 0.2% to 0.9%, more preferably 0.2% to 0.7%, even more preferably 0.2% to 0.5% and yet more preferably 0.3% to 0.5%, as the percentage of atoms based on the total number of lithium atoms (atomic number: 3) to uranium atoms (atomic number: 92) on the surfaces of the beads for blood processing. The ratio of the number of nitrogen atoms on the surfaces of the beads for blood processing is preferably within this range, since it will allow the beads for blood processing to have high blood compatibility while adsorbing hydrophobic protein molecules. The ratio of nitrogen atoms on the surfaces of the beads for blood processing can be adjusted by using a nitrogen-containing biocompatible polymer. For the first embodiment, for example, the charged monomer used may be a nitrogen-containing monomer, and the other monomer used may be another nitrogen-containing monomer, or both (also to be collectively referred to as "nitrogen-containing monomer"). For the second embodiment, the zwitterionic monomer used may be a nitrogen-containing zwitterionic monomer, and the other monomer used may be another nitrogen-containing monomer, or both (also to be collectively referred to as "nitrogen-containing monomer"). More specifically, the ratio of nitrogen atoms on the surfaces of the beads for blood processing can be adjusted by (1) adjusting the ratio of nitrogen-containing monomer composing the biocompatible polymer, and/or (2) adjusting the supported amount of nitrogen-containing biocompatible polymer on the porous beads. The sum of the ratio of carbon atoms and oxygen atoms on the surfaces of the beads for blood processing is preferably 97.0% or higher, as the percentage of atoms based on the total number of lithium atoms (atomic number: 3) to uranium atoms (atomic number: 92) on the surfaces of the beads for blood processing. The ratio of phosphorus atoms on the surfaces of the beads for blood processing is preferably 3% or lower and more preferably 1% or lower, as the percentage of atoms based on the total number of lithium atoms (atomic number: 3) to uranium atoms (atomic number: 92) on the surfaces of the beads for blood processing.

The ratio of specific atoms on the surfaces of the beads for blood processing can be measured by X-ray photoelectron spectroscopy (XPS). The measuring method is described in detail below under "Examples".

By pulverizing the beads for blood processing into powder and measuring the powder surface by XPS, it is possible to measure the ratio of specific atoms composing the beads for blood processing, based on the total number of atoms with atomic numbers of 3 to 92. The ratio of nitrogen atoms composing the beads for blood processing, as measured in this manner, is preferably higher than 0% and 0.1% or lower, based on the total number of atoms with atomic numbers of 3 to 92. The ratio of phosphorus atoms composing the beads for blood processing, as measured in this manner, is preferably 0.1% or lower, based on the total number of atoms with atomic numbers of 3 to 92. The ratios of nitrogen atoms and phosphorus atoms are preferably each within this range, since this will allow the beads for blood processing to have high blood compatibility while adsorbing hydrophobic protein molecules.

<Adsorption of Beads for Blood Processing>

When hydrophobic protein molecules of greater than 1000 Da and less than 66,000 Da are removed from blood with the beads for blood processing of this embodiment, the adsorption property of the porous beads supporting the polymer can be further improved and the eluting biocompatible polymer can be more effectively adsorbed in the pores. This range is therefore preferred in order to make it possible to obtain beads for blood processing with more satisfactory blood compatibility and reduced elution of the biocompatible polymer into blood. For the current purpose, the ability to "remove" a hydrophobic protein molecule means that when a blood plasma sample containing a hydrophobic protein molecule to be removed is contacted and agitated with the beads for blood processing, the adsorption rate of the hydrophobic protein onto the beads for blood processing is 30% or higher. The method of evaluating the adsorption property of the beads for blood processing is described below under "Examples". The beads for blood processing of this embodiment are capable of removing hydrophobic protein molecules with sizes of more preferably greater than 8000 Da and less than 66,000 Da, and even more preferably greater than 8000 Da and less than 51,000 Da. For example, cytokines have molecular weights of approximately 5 to 60 kDa (IL-1b: ~17.5 kDa, IL-6: ~24.5 kDa, IL-8: ~8 kDa, IL-10 (dimer): ~37.5 kDa, TNF-α (trimer): ~51 kDa), and the high-mobility group box 1 (HMGB1) alarmin is a hydrophobic protein with a molecular weight of approximately 30 kDa.

Hydrophobic protein molecules to be removed include protein molecules considered to be causes of sepsis, such as PAMPs (pathogen-associated molecular patterns) which are exogenous substances from pathogenic microorganisms; and inflammatory mediators associated with the inflammatory response, such as alarmins that are endogenous substances released by tissue damage, and cytokines that elicit an inflammatory response. Leukocytes are also included as hydrophobic protein molecules.

Examples of PAMPs include endotoxins (LPS), peptidoglycans (PGN), lipoteichoic acid, double stranded RNA (dsRNA) and flagellins.

Examples of alarmins include high-mobility group box 1 (HMGB1), heat shock proteins (HSPs), histones, fibrinogen, neutrophil elastase and macrophage inhibitory factor (MIF).

Examples of cytokines include interleukins (IL-1, IL-2, IL-3, IL-4, IL-5, IL-6, IL-7, IL-8, IL-9, IL-10, IL-11, IL-12, IL-13, IL-14, IL-15, IL-16, IL-17 and IL-18), and tumor necrosis factors (TNF-α and TNF-β).

Of these, the beads for blood processing are preferably used to remove alarmins and cytokines, and more preferably are used to remove HMGB1 and cytokines.

<Biocompatibility of Beads for Blood Processing>

The beads for blood processing of this embodiment also have excellent biocompatibility, in addition to the maintaining adsorption properties as mentioned above. The meaning of the term "biocompatibility" differs depending on the purpose and method of using a particular blood purification device, but for the purpose of the present specification, the index of biocompatibility that is used is the degree of adhesion of platelets onto the beads for blood processing. Greater inhibition of platelet adhesion onto the beads for blood processing is considered to be superior biocompatibility of the beads for blood processing. The method of evaluating the platelet adhesion of the beads for blood processing is described below under "Examples".

With the beads for blood processing of the first embodiment, the platelet adsorption rate onto the porous beads is preferably 0.1% to 30%, more preferably 0.3% to 20% and even more preferably 0.5% to 11%, as measured by the evaluation method for "platelet adhesion of the beads for blood processing", described in detail below under "Examples". For example, when using porous beads composed of an acrylic-based resin, the adhesion is preferably 0.1% to 22%, more preferably 0.3% to 13% and even more preferably 0.5% to 9%. When using porous beads composed of a styrene-based resin, for example, the adhesion is preferably 0.5% to 30%, more preferably 1% to 22% and even more preferably 3% to 11%.

With the beads for blood processing of the second embodiment, the platelet residue rate onto the porous beads is preferably 81% to 100%, more preferably 83% to 95% and even more preferably 85% to 95%, as measured by the evaluation method for "Platelet adhesion of beads for blood processing", described in detail below under "Examples".

<Method for Producing Beads for Blood Processing>

The method for producing beads for blood processing for this embodiment is not limited. For example, the method for producing beads for blood processing of this embodiment includes supporting the biocompatible polymer of this embodiment on the surfaces of porous beads composed of at least one resin selected from the group consisting of acrylic-based resins, styrene-based resins and cellulose-based resins. The details regarding the biocompatible polymer and monomers of this embodiment were explained above and will not be repeated here.

<Method for Producing Biocompatible Polymer>

The method of producing the biocompatible polymer for the first embodiment is not limited. For example, the method for producing the biocompatible polymer includes preparing a monomer solution containing a monomer of formula (1) in a desired solvent, adding a desired polymerization initiator to the monomer solution to prepare a polymerization solution, and polymerizing the monomer.

A charged monomer may also be added to the monomer solution and/or the polymerization solution in addition to the monomer of formula (1), and copolymerized with the monomer of formula (1). The charged monomer was described in detail above and will not be described again here.

The method of producing the biocompatible polymer for the second embodiment is not limited. For example, the method for producing the biocompatible polymer includes preparing a monomer solution containing a zwitterionic monomer in a desired solvent, adding a desired polymerization initiator to the monomer solution to prepare a polymerization solution, and polymerizing the monomer.

A monomer of formula (4) may also be added to the monomer solution and/or the polymerization solution in addition to the zwitterionic monomer, and copolymerized with the zwitterionic monomer. The monomer of formula (4) was described in detail above and will not be described again here.

For this embodiment, the polymerized biocompatible polymer may be purified by any purification process such as reprecipitation, dialysis, ultrafiltration or extraction. The purified biocompatible polymer may also be dried by any drying method such as reduced pressure drying, spray-drying, freeze-drying or heated air drying.

<Method of Supporting Biocompatible Polymer>

The method of supporting the biocompatible polymer on the surfaces of the porous beads may be any supporting method such as coating, spraying or dipping.

Dipping, for example, includes preparing a coating solution of the biocompatible polymer dissolved in a desired solvent such as alcohol, chloroform, acetone, tetrahydrofuran or dimethylformamide, and dipping the porous beads in the coating solution. After impregnation, the porous beads may be removed from the coating solution and the excess solution removed, and then dried by a desired drying method. The drying method may be air-drying in dry air, or reduced pressure drying in which drying is carried out in a reduced pressure atmosphere at ordinary temperature or while heating. Reduced pressure drying is preferred from the viewpoint of reducing the amount of polymer per 1 g of porous beads for this embodiment.

Coating or spraying includes such drying, for example, after the coating solution has been coated or sprayed onto the porous beads.

<Blood Purification Device>

A blood purification device of this embodiment has beads for blood processing according to the embodiment. The blood purification device will generally have a main body container with a blood inlet, an interior space and a blood outlet, the interior space being able to store the beads for blood processing. During blood purification treatment, usually the blood prior to treatment is introduced into the interior space through the blood inlet and is treated by contact with the beads for blood processing of this embodiment that are present inside the interior space, while allowing the treated blood to flow out through the blood outlet.

The shape of the main body container is not restricted, and it may be tubular, or more typically cylindrical columnar, for example.

The material composing the main body container is also not restricted, and it may be a thermoplastic resin such as polypropylene, polyethylene, polyester, polystyrene, polyethylene tetrafluoride, polycarbonate, acrylonitrile-butadiene-styrene (ABS), or a copolymer comprising a vinylaromatic hydrocarbon and a conjugated diene. A thermosetting resin such as a polyurethane or epoxy resin may also be used for sealing.

EXAMPLES

Embodiments of the invention will now be explained in detail through examples and comparative examples, with the understanding that these examples and comparative examples are not limitative on the invention.

<Measurement of Physical Properties of Porous Beads>
<Volume-Average Particle Size of Porous Beads>

The sizes of porous beads swelled with ultrapure water were measured, for 2000 beads, using a digital microscope VHX-900 (product of Keyence Corp.), and their volume average was calculated as the volume-average particle size (m).

<Cumulative Pore Capacity of Porous Beads>

The porous beads swelled with ultrapure water were frozen and then freeze-dried for 24 hours to dry the porous beads, after which a VacPrep061 (product Shimadzu Corp.-Micromeritics) was used for degassing treatment (reduced pressure drying) for 15 hours at 60° C. A TriStarII 3020 (product of Shimadzu Corp.-Micromeritics) was then used to measure the cumulative pore capacity ($cm^3/g$) by the N2 gas adsorption method. The Desorption Cumulative Pore Volume determined by the BJH method was used as the cumulative pore capacity.

<Area-to-Weight Ratio of Porous Beads>

The dried beads for blood processing were subjected to degassing treatment (reduced pressure drying) for 15 hours at 60° C. using a VacPrep061 (product of Shimadzu Corp.-Micromeritics). A TriStarII 3020 (product of Shimadzu Corp.-Micromeritics) was then used to measure the area-to-weight ratio ($m^2/g$) by the $N_2$ gas adsorption method. The value from a BET plot was used as the area-to-weight ratio.

<Measurement of Physical Properties of Coated Beads>
<Measurement of Elution of Coated Beads>

A 100 mL conical beaker and weighing bottle were adequately washed with ultrapure water and thoroughly dried. The weight of the dried weighing bottle was measured just before use (this will be referred to as "weight of weighing bottle before treatment"). After adding 5.0 mL of coated beads (1.10 g dry weight) into a 100 mL conical beaker, 50 mL of ultrapure water was added (this solution will be referred to as "sample solution"). Separately, 50 mL of ultrapure water alone was also added to a 100 mL conical beaker (this solution will be referred to as "blank solution"). Next, the tops of the two different beakers were completely covered with aluminum foil, while simultaneously carrying out autoclave sterilization treatment (LSX-500L, product of Tomy Seiko Co., Ltd.) at 121° C. for 20 minutes. After cooling the two autoclave sterilized beakers to room temperature, the solutions in the beakers were filtered using filter paper (ADVANTEC, No. 5C), and they were transferred to fresh 100 mL conical beakers. The two obtained filtered solutions were placed in separate weighing bottles in an amount of 20 mL each, and the moisture of the solutions in the weighing bottles were evaporated off on a hot plate. The weighing bottles were then further dried at 105° C. for 1 hour in a hot air drier (DN4101, Yamato Corp.), and the weights of the dried weighing bottles were measured (this will be referred to as "treated weighing bottle weight").

The amounts of evaporation residue of the sample solution, evaporation residue of the blank solution, and eluate of the coated beads, were calculated by the following formulas. When the evaporation residue calculated for the blank solution was 0.3 mg or lower, the value of the amount of eluate of the coated beads was used. The value of the amount of eluate of the coated beads was measured twice and calculated, judging the elution to be high when the average value exceeded 1.0 mg, and judging the elution to be low when it was 1.0 mg or lower.

Sample solution evaporation residue (mg)=Treated weighing bottle weight (mg)−weight of weighing bottle before treatment (mg)

Blank solution evaporation residue (mg)=Treated weighing bottle weight (mg)−weight of weighing bottle before treatment (mg)

Coated beads elution (mg)=Sample solution evaporation residue (mg)−blank solution evaporation residue (mg)

1. Examples and Comparative Examples for First Embodiment

Example 1-1

<Synthesis of Coating Polymer>

A copolymer of 2-methoxyethyl methacrylate (MEMA, compound of structural formula (i) in [Chemical Formula 9]), N,N-diethylaminoethyl methacrylate (DEAEMA, compound of structural formula (ii) in [Chemical Formula 9]) and N-methacryloyloxyethyl-N,N-dimethylammonium-α-N-methylcarboxybetaine (CMB, compound of structural formula (iii) in [Chemical Formula 9]) was synthesized by common solution polymerization. The polymerization conditions were a concentration of 1 mol/L for each monomer, in an ethanol solution in the presence of 0.0025 mol/L of azoisobutyronitrile (AIBN) as an initiator, and polymerization reaction was conducted for 8 hours at a reaction temperature of 60° C., to obtain a polymer solution. The obtained polymer solution was dropped into diethyl ether and the precipitated polymer was recovered. The recovered polymer was purified by a reprecipitation procedure using diethyl ether. The obtained polymer was then dried for 24 hours under reduced pressure conditions to obtain a coating polymer.

The molar ratio of the MEMA monomer unit, the DEAEMA monomer unit and the CMB monomer unit in the coating polymer was measured in the following manner. The obtained coating polymer was dissolved in dimethyl sulfoxide, and then calculation was performed by the following formula from the peak at 4.32 ppm (from H atoms unique to CMB) and the peak at 2.63 ppm (from H atoms unique to DEAEMA), in a chart calculated after carrying out $^1$H-NMR measurement, and the area ratio at 0.65 to 2.15 ppm (total H atoms).

DEAEMA monomer molar ratio=("Area ratio in 2.63 ppm range"/2)/("area ratio in 0.65 to 2.15 ppm range"/5−"area ratio in 2.63 ppm range"×0.3)×100

CMB monomer molar ratio=("Area ratio in 4.32 ppm range"/2)/("area ratio in 0.65 to 2.15 ppm range"/5−"area ratio in 2.63 ppm range"×0.3)×100

MEMA monomer molar ratio=100−DEAEMA monomer molar ratio−CMB monomer molar ratio

The molar ratio of the MEMA monomer unit, the DEAEMA monomer unit and the CMB monomer unit for the coating polymer was calculated to be 80/10/10.

<Preparation of Coating Solution>

After adding the coating polymer to 70 W/W % ethyl alcohol, the mixture was stirred for 12 hours to prepare a coating solution with a coating polymer concentration of 0.1 wt %.

<Preparation of Beads>

Figure 3:
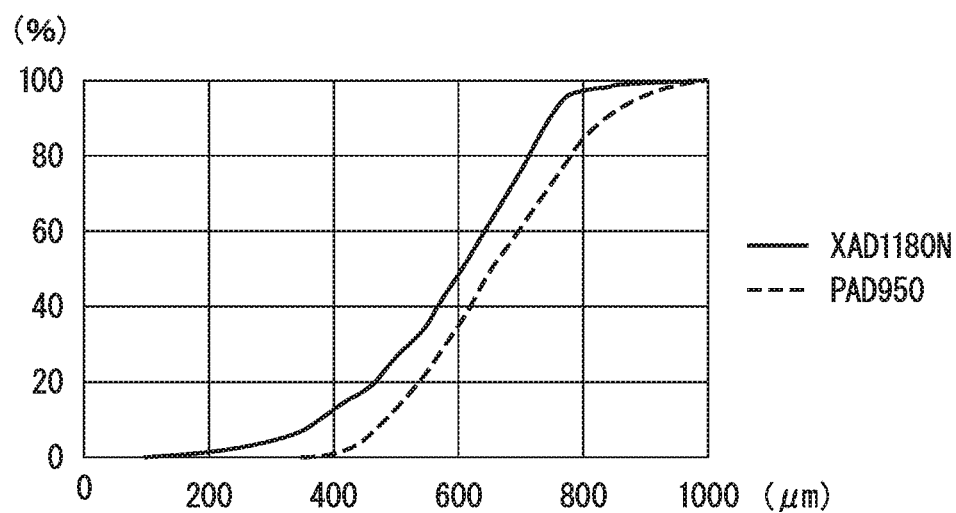
FIG. 3 is a graph showing cumulative volume particle size distribution for AMBERLITE™ XAD™ 1180N and PuroSorb™ PAD950.

The porous beads used were AMBERLITE™ XAD™ 1180N (product of Organo Co., Ltd., styrene-based polymer beads, volume-average particle size: 609 μm, cumulative pore capacity of 1.472 $cm^3/g$ for pore sizes of 5 nm to 100 nm, cumulative pore capacity of 0.020 cm³/g for pore sizes of 100 nm to 200 nm). A graph of the log differential pore volume distribution and cumulative pore capacity of AMBERLITE™ XAD™ 1180N is shown in FIG. 1, and a graph of the cumulative volume particle size distribution is shown in FIG. 3. After placing 2 mL of ultrapure water-swelled beads (0.44 g dry weight) in a 15 mL polypropylene (PP) conical tube, 10 mL of 70 W/W % ethyl alcohol was added. A shaker (InVitro Shaker WAVE-S1, product of Taitec Co.) was used for 12 hours of shaking at 40 r/min at a shaking angle of 10 degrees, and then the shaken solution was filtered with a cell strainer (Mini Cell Strainer II, 70 μm nylon mesh, product of Funakoshi Corp.). After measuring the absorbance of the filtered solution at 220 nm using a Shimadzu UV-2600 Ultraviolet-visible spectrophotometer (product of Shimadzu Corp.), the filtered beads were again added to a 15 mL conical tube. The procedure including addition of 70 W/W % ethyl alcohol to the conical tube, shaking for 12 hours with the shaker and solution removal with the cell strainer was repeated until the absorbance of the filtered solution at 220 nm reached 0.03 or lower.

<Coating Method>

After adding 10 mL of the coating solution to the 15 mL conical tube containing 2 mL of the treated beads, a shaker (InVitro Shaker WAVE-S1, product of Taitec Co.) was used for shaking at 40 r/min for 3 hours at a shaking angle of 10 degrees. The coated solution was then filtered with a cell strainer (Mini Cell Strainer II, 70 μm nylon mesh, product of Funakoshi Corp.) to obtain coated beads. After measuring the absorbance of the filtered coated solution at 220 nm using a Shimadzu UV-2600 Ultraviolet/visible spectrophotometer (product of Shimadzu Corp.), the filtered coated beads were again added to a 15 mL conical tube. The coating amount on the beads (mg/g dry beads) was calculated by the following formula and found to be a coating polymer coating amount of 6 mg/g dry beads.

Coating polymer weight in treated solution (mg)
=Coating polymer weight in untreated solution (mg)×absorbance of treated solution at 220 nm/absorbance of untreated solution at 220 nm Coating amount (mg/g dry beads)=(Coating polymer weight in untreated solution−coating polymer weight in treated solution)/g dry beads used After then vacuum drying the 15 mL conical tube containing the coated beads for 15 hours at 50° C. (absolute pressure: ≤0.003 MPa), 12 mL of 20 W/W % ethyl alcohol was added to the conical tube. A shaker (InVitro Shaker WAVE-S1, product of Taitec) was used for shaking at 40 r/min for 12 hours at a shaking angle of 10°, and then the solution in which the beads were swelled was removed with a cell strainer (Mini Cell Strainer II, 70 μm nylon mesh, product of Funakoshi Corp.), and the resulting beads were again added to a 15 mL conical tube. The procedure of addition of 12 mL of ultrapure water to the 15 mL conical tube, shaking for 3 hours with the shaker and solution removal with the cell strainer was then repeated a total of 5 times. Finally, the conical tube was filled with 12 mL of physiological saline (Otsuka Normal Saline, product of Otsuka Pharmaceutical Factory, Inc.), and sterilization was carried out with γ-ray irradiation to obtain beads for blood processing.

<Overall Elemental Analysis of Beads for Blood Processing>

The solution in 1 mL of the beads for blood processing was removed with a cell strainer, and the resulting beads were added to a 15 mL conical tube. Next, 12 mL of ultrapure water was added to the 15 mL conical tube to replace the bead solution with ultrapure water. The beads for blood processing replaced with ultrapure water were vacuum dried for 15 hours at 50° C. (absolute pressure: 0.003 MPa). The dried beads for blood processing were subjected to elemental analysis using an elemental analyzer (EMGA-930 oxygen/nitrogen/hydrogen analyzer by Horiba, Ltd.). The analysis was conducted with 3 samples, and the average value was recorded. The nitrogen element ratio was found to be ≤0.3 weight %.

<XPS Measurement of Surfaces of Beads for Blood Processing>

After randomly selecting 50 of the dried beads for blood processing, the surface condition of each bead was measured by XPS using a K-Alpha+ (product of Thermo Fisher Scientific). The measuring conditions were: Irradiated x-rays: single crystal spectroscopy Al Kα, X-ray spot diameter: 150 μm, neutralizing electron gun: used. The averaged value for the abundance ratio of nitrogen atoms with respect to the total number of lithium atoms (atomic number: 3) to uranium atoms (atomic number: 92) on the surfaces of the 50 beads for blood processing was calculated as the abundance ratio (%) of nitrogen atoms on the surfaces of the beads for blood processing. The results are shown in Table 3.

<XPS Measurement of Entirety of Beads for Blood Processing>

The dried beads for blood processing were ground with a pestle to prepare powder of the beads for blood processing. The surface condition of the powder was measured by XPS using a K-Alpha+ (product of Thermo Fisher Scientific). The measuring conditions were: Irradiated x-rays: single crystal spectroscopy Al Kα, X-ray spot diameter: 150 μm, neutralizing electron gun: used. The measurement was conducted for 10 samples, and the averaged value for the abundance ratio of nitrogen atoms with respect to the total number of lithium atoms (atomic number: 3) to uranium atoms (atomic number: 92) was calculated as the abundance ratio (%) of nitrogen atoms for the entirety of the beads for blood processing. The results are shown in Table 3.

<Adsorption of Beads for Blood Processing>

Heparin sodium (heparin sodium injection, 50,000 unit/50 mL, product of Nipro Corp.) was added to blood collected from a healthy volunteer, to a concentration of 2000 IU/mL, and then *Escherichia coli* O111:B4-derived lipopolysaccharide (LPS) (product of Sigma-Aldrich) was added to a concentration of 0.1 μg/mL and a shaker (InVitro Shaker WAVE-S1, product of Taitec) was used for shaking at 10 r/min for 24 hours at 37° C., with a shaking angle of 10 degrees. A centrifuge (6200 Hybrid high-speed refrigerated centrifuge, product of Kubota Corp.) was then used for centrifugation at 2000 g for 20 minutes at room temperature, and the supernatant was obtained as the blood plasma sample. After mixing 3.6 mL of the obtained blood plasma sample and 0.45 mL of the beads for blood processing (0.10 g dry weight) in a 5 mL polypropylene (PP) tube, a shaker was used for shaking at 10 r/min for 2 hours at 37° C., with a shaking angle of 10 degrees (for use as a bead-contact sample). A sample was also prepared without addition of beads in 3.6 mL of the obtained blood plasma sample, and was treated in the same manner as the bead-contact sample (for use as the non-bead-contact sample). The shaken PP tube was centrifuged at 2000 g for 1 minute at room temperature using a centrifuge, to obtain supernatants of the bead-contact and non-bead-contact samples. The supernatants were used for measurement of different cytokine concentrations using a Bio-Plex system (product of Bio-Rad, Bio-Plex Pro human cytokine G127-plex panel), according to the manufacturer's instruction manual. The HMGB-1 concentration was measured using an HMGB1 ELISAK Kit II (product of Shino-Test Corp.), according to the manufacturer's instruction manual. The cytokine and HMGB-1 adsorption rates of the beads were calculated by the following formulas. The results are shown in Table 1.

Cytokine adsorption rate (%)=("Cytokine concentration of non-bead-contact sample"−"cytokine concentration of bead-contact sample")/"cytokine concentration of non-bead-contact sample"×100

HMGB-1 adsorption rate (%)=("HMGB-1 concentration of non-bead-contact sample"−"HMGB-1 concentration of bead-contact sample")/"HMGB-1 concentration of non-bead-contact sample"×100

The cytokine concentrations for the non-bead-contact sample and the HMGB-1 concentration for the non-bead-contact sample for this experiment were IL-1b: 3658 pg/mL, IL-6: 5540 pg/mL, IL-8: 6144 pg/mL, IL-10: 846 pg/mL, TNF-α: 8085 pg/mL and HMGB-1: 27 ng/mL.

<Platelet Adhesion of Beads for Blood Processing>

Heparin sodium (heparin sodium injection, 50,000 unit/50 mL, product of Nipro Corp.) was added to blood collected from a healthy volunteer, to a concentration of 1200 IU/mL (this will be referred to as "untreated blood"). A 0.65 mL portion of the beads for blood processing (0.15 g dry weight) was mixed with 4.4 mL of the untreated blood in a 5 mL polypropylene (PP) tube. The tubes were attached in a radial fashion on a 20 cm-diameter discoid rotor of a ROTATOR RT-5 (product of Tietech Co., Ltd.), along the radial direction of the rotor. After setting the rotating surface of the discoid rotor at an angle of 22 with respect to the horizontal, rotational stirring was carried out at 37° C. for 3 hours at a speed of 4 rpm. The bead-contacted blood was then filtered with a cell strainer (Mini Cell Strainer II, 70 µm nylon mesh, product of Funakoshi Corp.), and the beads were removed (this will be referred to as "treated blood"). The platelet concentration of the treated blood was measured with an XT-1800i micro cell counter (product of Sysmex). The platelet adhesion rate onto the beads was calculated by the following formula, giving the results shown in Table 1.

Platelet adsorption rate (%)=(Platelet count of untreated blood−platelet count of treated blood)/ (platelet count of untreated blood)×100

The untreated blood used for this experiment had a leukocyte concentration of 4920/µL, an erythrocyte concentration of 430×10$^4$/µL, a platelet concentration of 240×10$^3$/µL and a hematocrit of 38.8%. The activation clotting time of the untreated blood was 304 seconds, as measured with a Hemochron Jr. Signature+ (product of International Technidyne Corp., JACT-LR Hemochron test cartridge).

Example 1-2

Beads for blood processing were prepared in the same manner as Example 1-1, except that the composition of the coating polymer was MEMA/DEAEMA/CMB=60/20/20 (molar ratio). Elemental analysis by the same method as in Example 1-1 showed the nitrogen element ratio to be ≤0.3 weight %. Table 1 shows the results of evaluating the platelet adhesion by the same method as in Example 1-1.

Example 1-3

Beads for blood processing were prepared in the same manner as Example 1-1, except that the composition of the coating polymer was MEMA/CMB=75/25 (molar ratio), and the coating amount of the coating polymer was 8 mg/g dry beads. Elemental analysis by the same method as in Example 1-1 showed the nitrogen element ratio to be ≤0.3 weight %. Table 1 shows the results of evaluating the cytokine adsorption performance and platelet adhesion, by the same methods as in Example 1-1. Table 3 shows the results of XPS measurement of the bead surfaces and XPS measurement of the entire beads, by the same methods as in Example 1-1.

Example 1-4

Beads for blood processing were prepared in the same manner as Example 1-1, except that the composition of the coating polymer was MEMA/CMB=75/25 (molar ratio), the coating polymer concentration of the coating solution used was 0.5 wt %, and the coating amount of the coating polymer was 31 mg/g dry beads. Elemental analysis by the same method as in Example 1-1 showed the nitrogen element ratio to be ≤0.3 weight %. Table 1 shows the results of evaluating the cytokine adsorption performance and platelet adhesion, by the same methods as in Example 1-1. Table 3 shows the results of XPS measurement of the bead surfaces and XPS measurement of the entire beads, by the same methods as in Example 1-1.

Example 1-5

Beads for blood processing were prepared in the same manner as Example 1-1, except that the composition of the coating polymer was MEMA/CMB=75/25 (molar ratio), the coating polymer concentration of the coating solution used was 0.033 wt %, and the coating amount of the coating polymer was 2.4 mg/g dry beads. Elemental analysis by the same method as in Example 1-1 showed the nitrogen element ratio to be ≤0.3 weight %. Table 1 shows the results of evaluating the cytokine adsorption performance and platelet adhesion, by the same methods as in Example 1-1. Table 3 shows the results of XPS measurement of the bead surfaces and XPS measurement of the entire beads, by the same methods as in Example 1-1.

Example 1-6

Beads for blood processing were prepared in the same manner as Example 1-1, except that the composition of the coating polymer was MEMA/DEAEMA=80/20 (molar ratio), and the coating amount of the coating polymer was 10 mg/g dry beads. Elemental analysis by the same method as in Example 1-1 showed the nitrogen element ratio to be ≤0.3 weight %. Table 1 shows the results of evaluating the platelet adhesion by the same method as in Example 1-1. Table 3 shows the results of XPS measurement of the bead surfaces and XPS measurement of the entire beads, by the same methods as in Example 1-1.

Example 1-7

Beads for blood processing were prepared in the same manner as Example 1-1, except that the composition of the coating polymer was MEMA/DEAEMA/AAc (acrylic acid, compound of structural formula (iv) in [Chemical Formula 9])=60/28/12 (molar ratio), and the coating amount of the coating polymer was 8 mg/g dry beads. Elemental analysis by the same method as in Example 1-1 showed the nitrogen element ratio to be ≤0.3 weight %. Table 1 shows the results of evaluating the platelet adhesion by the same method as in Example 1-1.

Example 1-8

Beads for blood processing were prepared in the same manner as Example 1-1, except that the composition of the coating polymer was MEMA/DEAEMA/AAc=71/15/14 (molar ratio), and the coating amount of the coating polymer was 5 mg/g dry beads. Elemental analysis by the same method as in Example 1-1 showed the nitrogen element ratio to be ≤0.3 weight %. Table 1 shows the results of evaluating the cytokine adsorption performance and platelet adhesion, by the same methods as in Example 1-1. Table 3 shows the results of XPS measurement of the bead surfaces and XPS measurement of the entire beads, by the same methods as in Example 1-1.

Example 1-9

Beads for blood processing were prepared in the same manner as Example 1-1, except that the composition of the coating polymer was MEMA/DEAEMA/MAc (methacrylic acid, compound of structural formula (v) in [Chemical Formula 9])=62/15/23 (molar ratio), and the coating amount of the coating polymer was 4 mg/g dry beads. Elemental analysis by the same method as in Example 1-1 showed the nitrogen element ratio to be ≤0.3 weight %. Table 1 shows the results of evaluating the cytokine adsorption performance and platelet adhesion, by the same methods as in Example 1-1.

Example 1-10

Beads for blood processing were prepared in the same manner as Example 1-1, except that the composition of the coating polymer was MEMA=100 (molar ratio), and the coating amount of the coating polymer was 11 mg/g dry beads. Elemental analysis by the same method as in Example 1-1 showed the nitrogen element ratio to be ≤0.3 weight %. Table 1 shows the results of evaluating the cytokine adsorption performance and platelet adhesion, by the same methods as in Example 1-1.

Example 1-11

Beads for blood processing were prepared in the same manner as Example 1-1, except that the composition of the coating polymer was BMA (n-butyl methacrylate, compound of structural formula (vi) in [Chemical Formula 9])/DEAEMA/CMB=80/10/10 (molar ratio), the coating polymer solution used was 100 W/W % ethyl alcohol instead of 70 W/W % ethyl alcohol, and the coating amount of the coating polymer was 4 mg/g dry beads. Elemental analysis by the same method as in Example 1-1 showed the nitrogen element ratio to be ≤0.3 weight %. Table 1 shows the results of evaluating the platelet adhesion by the same method as in Example 1-1.

Example 1-12

Beads for blood processing were prepared in the same manner as Example 1-1, except that the composition of the coating polymer was BMA/CMB=70/30 (molar ratio), and the coating amount of the coating polymer was 6 mg/g dry beads. Elemental analysis by the same method as in Example 1-1 showed the nitrogen element ratio to be ≤0.3 weight %. Table 1 shows the results of evaluating the platelet adhesion by the same method as in Example 1-1. Table 3 shows the results of XPS measurement of the bead surfaces and XPS measurement of the entire beads, by the same methods as in Example 1-1.

Example 1-13

Beads for blood processing were prepared in the same manner as Example 1-1, except that the composition of the coating polymer was LMA (lauryl methacrylate, compound of structural formula (vii) in [Chemical Formula 9])/DEAEMA/CMB=80/10/10 (molar ratio), the coating polymer solution used was 100 W/W % n-butyl alcohol instead of 70 W/W % ethyl alcohol, and the coating amount of the coating polymer was 4 mg/g dry beads. Elemental analysis by the same method as in Example 1-1 showed the nitrogen element ratio to be ≤0.3 weight %. Table 1 shows the results of evaluating the platelet adhesion by the same method as in Example 1-1.

Example 1-14

Beads for blood processing were prepared in the same manner as Example 1-1, except that the composition of the coating polymer was LMA/DEAEMA/CMB=60/20/20 (molar ratio), the coating polymer solution used was 100 W/W % n-butyl alcohol instead of 70 W/W % ethyl alcohol, and the coating amount of the coating polymer was 4 mg/g dry beads. Elemental analysis by the same method as in Example 1-1 showed the nitrogen element ratio to be ≤0.3 weight %. Table 1 shows the results of evaluating the platelet adhesion by the same method as in Example 1-1.

Example 1-15

Beads for blood processing were prepared in the same manner as Example 1-1, except that the composition of the coating polymer was LMA/DEAEMA/CMB=40/30/30 (molar ratio) and the coating polymer solution used was 100 W/W % ethyl alcohol instead of 70 W/W % ethyl alcohol. Elemental analysis by the same method as in Example 1-1 showed the nitrogen element ratio to be ≤0.3 weight %. Table 1 shows the results of evaluating the platelet adhesion by the same method as in Example 1-1. Table 3 shows the results of XPS measurement of the bead surfaces and XPS measurement of the entire beads, by the same methods as in Example 1-1.

Example 1-16

Beads for blood processing were prepared in the same manner as Example 1-1, except that the composition of the coating polymer was LMA/CMB=70/30 (molar ratio), the coating polymer solution used was 100 W/W % ethyl alcohol instead of 70 W/W % ethyl alcohol, and the coating amount of the coating polymer was 5 mg/g dry beads. Elemental analysis by the same method as in Example 1-1 showed the nitrogen element ratio to be ≤0.3 weight %. Table 1 shows the results of evaluating the platelet adhesion by the same method as in Example 1-1.

Example 1-17

Beads for blood processing were prepared in the same manner as Example 1-1, except that the composition of the coating polymer was MEMA/CMB=85/15 (molar ratio), and the coating amount of the coating polymer was 9 mg/g dry beads. Elemental analysis by the same method as in Example 1-1 showed the nitrogen element ratio to be ≤0.3 weight %. Table 1 shows the results of evaluating the platelet adhesion by the same method as in Example 1-1.

Example 1-18

Beads for blood processing were prepared in the same manner as Example 1-1, except that the composition of the coating polymer was MEMA/MPC (2-(methacryloyloxy) ethyl 2-(trimethylammonio)ethyl phosphate, compound of structural formula (viii) in [Chemical Formula 9])=85/15 (molar ratio), and the coating amount of the coating polymer was 7 mg/g dry beads. Elemental analysis by the same method as in Example 1-1 showed the nitrogen element ratio to be ≤0.3 weight %. Table 1 shows the results of evaluating the platelet adhesion by the same method as in Example 1-1. Table 3 shows the results of XPS measurement of the bead surfaces and XPS measurement of the entire beads, by the same methods as in Example 1-1.

Example 1-19

Beads for blood processing were prepared in the same manner as Example 1-1, except that the composition of the coating polymer was MEMA/DMAEMA (dimethylaminoethyl methacrylate, compound of structural formula (ix) in [Chemical Formula 9])=80/20 (molar ratio), and the coating amount of the coating polymer was 9 mg/g dry beads. Elemental analysis by the same method as in Example 1-1 showed the nitrogen element ratio to be ≤0.3 weight %. Table 1 shows the results of evaluating the platelet adhesion by the same method as in Example 1-1.

Example 1-20

Figure 2:
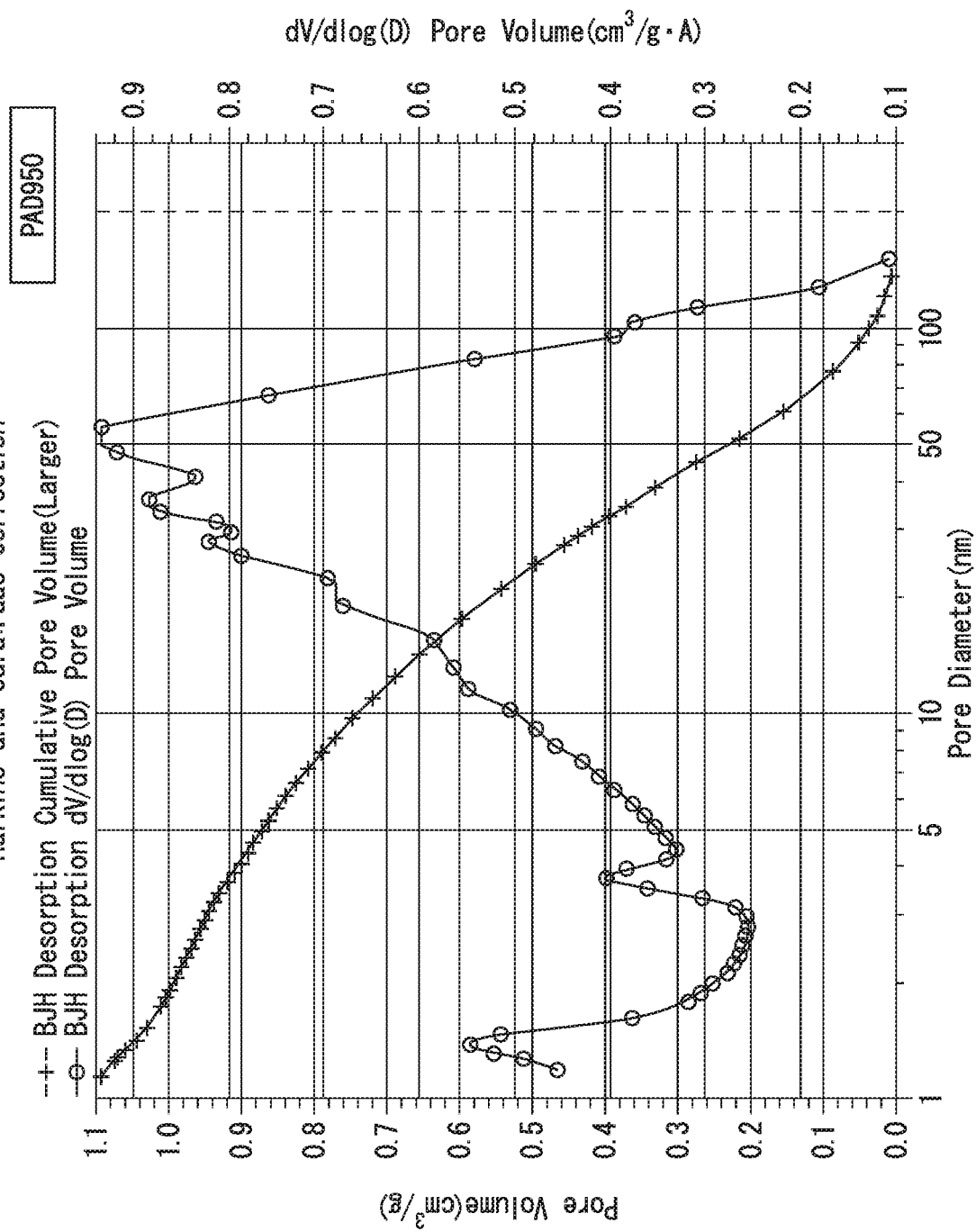
FIG. 2 is a graph showing log differential pore volume distribution and cumulative pore capacity for PuroSorb™ PAD950 (acrylic beads by Purolite Corp.).

Beads for blood processing were prepared in the same manner as Example 1-1, except that the beads selected were PuroSorb™ PAD950 (product of Purolite Corp., acrylic polymer beads, volume-average particle size: 621 μm, cumulative pore capacity for pore sizes of 5 nm to 100 nm: 0.823 cm³/g, cumulative pore capacity for pore sizes of 100 nm to 200 nm: 0.038 cm³/g) instead of AMBERLITE™ XAD™ 1180N, and the coating amount of the coating polymer was 14 mg/g dry beads. A graph of the log differential pore volume distribution and cumulative pore capacity of PuroSorb™ PAD950 is shown in FIG. 2, and a graph of the cumulative volume particle size distribution is shown in FIG. 3. Elemental analysis by the same method as in Example 1-1 showed the nitrogen element ratio to be ≤0.3 weight %. Table 2 shows the results of evaluating the platelet adhesion by the same method as in Example 1-1. Table 3 shows the results of XPS measurement of the bead surfaces and XPS measurement of the entire beads, by the same methods as in Example 1-1.

Example 1-21

Beads for blood processing were prepared in the same manner as Example 1-2, except that the beads selected were PuroSorb™ PAD950 instead of AMBERLITE™ XAD™ 1180N, and the coating amount of the coating polymer was 13 mg/g dry beads. Elemental analysis by the same method as in Example 1-1 showed the nitrogen element ratio to be ≤0.3 weight %. Table 2 shows the results of evaluating the platelet adhesion by the same method as in Example 1-1.

Example 1-22

Beads for blood processing were prepared in the same manner as Example 1-3, except that the beads selected were PuroSorb™ PAD950 instead of AMBERLITE™ XAD™ 1180N, and the coating amount of the coating polymer was 6 mg/g dry beads. Elemental analysis by the same method as in Example 1-1 showed the nitrogen element ratio to be ≤0.3 weight %. Table 2 shows the results of evaluating the cytokine adsorption performance and platelet adhesion, by the same methods as in Example 1-1. Table 3 shows the results of XPS measurement of the bead surfaces and XPS measurement of the entire beads, by the same methods as in Example 1-1.

Example 1-23

Beads for blood processing were prepared in the same manner as Example 1-4, except that the beads selected were PuroSorb™ PAD950 instead of AMBERLITE™ XAD™ 1180N, and the coating amount of the coating polymer was 19 mg/g dry beads. Elemental analysis by the same method as in Example 1-1 showed the nitrogen element ratio to be ≤0.3 weight %. Table 2 shows the results of evaluating the cytokine adsorption performance and platelet adhesion, by the same methods as in Example 1-1.

Example 1-24

Beads for blood processing were prepared in the same manner as Example 1-6, except that the beads selected were PuroSorb™ PAD950 instead of AMBERLITE™ XAD™ 1180N, and the coating amount of the coating polymer was 16 mg/g dry beads. Elemental analysis by the same method as in Example 1-1 showed the nitrogen element ratio to be ≤0.3 weight %. Table 2 shows the results of evaluating the platelet adhesion by the same method as in Example 1-1.

Example 1-25

Beads for blood processing were prepared in the same manner as Example 1-7, except that the beads selected were PuroSorb™ PAD950 instead of AMBERLITE™ XAD™ 1180N, and the coating amount of the coating polymer was 13 mg/g dry beads. Elemental analysis by the same method as in Example 1-1 showed the nitrogen element ratio to be ≤0.3 weight %. Table 2 shows the results of evaluating the platelet adhesion by the same method as in Example 1-1.

Example 1-26

Beads for blood processing were prepared in the same manner as Example 1-10, except that the beads selected were PuroSorb™ PAD950 instead of AMBERLITE™ XAD™ 1180N, and the coating amount of the coating polymer was 15 mg/g dry beads. Elemental analysis by the same method as in Example 1-1 showed the nitrogen element ratio to be ≤0.3 weight %. Table 2 shows the results of evaluating the platelet adhesion by the same method as in Example 1-1.

Comparative Example 1-1

Beads for blood processing were prepared in the same manner as Example 1-1, except that the composition of the coating polymer was MEA (2-methoxyethyl acrylate, compound of structural formula (x) in [Chemical Formula 9])/DEAEMA/CMB=80/10/10 (molar ratio), the coating solution used had a coating polymer concentration of 0.3 wt %, and the coating amount of the coating polymer was 55 mg/g dry beads. Elemental analysis by the same method as in Example 1-1 showed the nitrogen element ratio to be ≤0.3 weight %. Table 1 shows the results of evaluating the cytokine adsorption performance and platelet adhesion, by the same methods as in Example 1-1. Table 3 shows the results of XPS measurement of the bead surfaces and XPS measurement of the entire beads, by the same methods as in Example 1-1.

Comparative Example 1-2

Beads for blood processing were prepared in the same manner as Example 1-1, except that the composition of the coating polymer was MEA/DEAEMA/CMB=80/10/10 (molar ratio), the coating polymer concentration of the coating solution used was 0.5 wt %, and the coating amount of the coating polymer was 94 mg/g dry beads. Elemental analysis by the same method as in Example 1-1 showed the nitrogen element ratio to be ≤0.3 weight %. Table 1 shows the results of evaluating the cytokine adsorption performance and platelet adhesion, by the same methods as in Example 1-1.

Comparative Example 1-3

Beads for blood processing were prepared in the same manner as Example 1-1, except that the composition of the coating polymer was BA (butyl acrylate, compound of structural formula (xi) in [Chemical Formula 9])=100 (molar ratio), and the coating amount of the coating polymer was 16 mg/g dry beads. Elemental analysis by the same method as in Example 1-1 showed the nitrogen element ratio to be ≤0.3 weight %. Table 1 shows the results of evaluating the platelet adhesion by the same method as in Example 1-1.

Comparative Example 1-4

Beads for blood processing were prepared in the same manner as Example 1-1, except that the composition of the coating polymer was BA/DEAEMA/CMB=60/20/20 (molar ratio), and the coating amount of the coating polymer was 12 mg/g dry beads. Elemental analysis by the same method as in Example 1-1 showed the nitrogen element ratio to be ≤0.3 weight %. Table 1 shows the results of evaluating the platelet adhesion by the same method as in Example 1-1.

Comparative Example 1-5

(Synthesis of Coating Polymer)
In a 3-necked volumetric flask there were added 7.50 g of 3-methoxypropyl acrylate (MC3A, compound of structural formula (xii) in [Chemical Formula 9]), 30.2 g of 1,4-dioxane and 7.5 mg of azobisisobutyronitrile (AIBN). The reaction mixture was stirred for 30 minutes while circulating dry nitrogen gas through, thus replacing the reaction system with nitrogen. It was then immersed in an oil bath with the bottom temperature of the three-necked volumetric flask set to 75° C., and polymerization was conducted by stirring under a nitrogen stream for 6 hours. Progression of the polymerization reaction was confirmed by 1H NMR, and after confirming a sufficiently high reaction conversion rate (~90%), the polymerization system was cooled to room temperature to halt the reaction. The polymerization solution was dropped into hexane to precipitate the polymer, the supernatant was removed by decantation, and the precipitate was dissolved in tetrahydrofuran and recovered. The procedure of dissolution in tetrahydrofuran and reprecipitation in hexane was repeated twice for purification, and the resulting precipitate was further stirred in water for 24 hours. The water was removed by decantation and the precipitate was dissolved in tetrahydrofuran and recovered. The solvent was distilled off under reduced pressure and then dried with a vacuum dryer to obtain a polymer. A portion of the obtained polymer was used to measure the molecular weight, which was found to be a number-average molecular weight (Mn) of 31,000 and a molecular weight distribution (Mw/Mn) of 2.5.

When the coating polymer was used for coating of beads by the same method as in Example 1-1, the coating amount was calculated to be 19 mg/g dry beads. Elemental analysis by the same method as in Example 1-1 showed the nitrogen element ratio to be ≤0.3 weight %. Table 1 shows the results of evaluating the platelet adhesion by the same method as in Example 1-1.

Comparative Example 1-6

Beads for blood processing were prepared in the same manner as Comparative Example 1-5, except that the coating polymer concentration of the coating solution used was 0.5 wt %, and the coating amount of the coating polymer was 91 mg/g dry beads. Elemental analysis by the same method as in Example 1-1 showed the nitrogen element ratio to be ≤0.3 weight %. Table 1 shows the results of evaluating the cytokine adsorption performance and platelet adhesion, by the same methods as in Example 1-1.

Comparative Example 1-7

(Synthesis of Coating Polymer)
Synthesis was carried out by the same method as in Comparative Example 1-5, except that polymerization was conducted for 10 hours at 75° C., with 15 g of 2-methoxyethyl acrylate (MEA), 60 g of 1,4-dioxane and 15 mg of azobisisobutyronitrile as the initiator. The results of GPC molecular weight analysis indicated a number-average molecular weight (Mn) of 20,000 and a molecular weight distribution (Mw/Mn) of 2.4.

When the coating polymer was used for coating of beads by the same method as in Example 1-1, the coating amount was calculated to be 21 mg/g dry beads. Elemental analysis by the same method as in Example 1-1 showed the nitrogen element ratio to be ≤0.3 weight %. Table 1 shows the results of evaluating the cytokine adsorption performance and platelet adhesion, by the same methods as in Example 1-1. Table 3 shows the results of XPS measurement of the bead surfaces and XPS measurement of the entire beads, by the same methods as in Example 1-1.

Comparative Example 1-8

Beads for blood processing were prepared in the same manner as Comparative Example 1-7, except that the coating polymer concentration of the coating solution used was 0.3 wt %, and the coating amount of the coating polymer was 56 mg/g dry beads. Elemental analysis by the same method as in Example 1-1 showed the nitrogen element ratio to be ≤0.3 weight %. Table 1 shows the results of evaluating the cytokine adsorption performance and platelet adhesion, by the same methods as in Example 1-1.

Comparative Example 1-9

Beads for blood processing were prepared in the same manner as Comparative Example 1-7, except that the coating polymer concentration of the coating solution used was 0.5 wt %, and the coating amount of the coating polymer was 97 mg/g dry beads. Elemental analysis by the same method as in Example 1-1 showed the nitrogen element ratio to be ≤0.3 weight %. Table 1 shows the results of evaluating the cytokine adsorption performance and platelet adhesion, by the same methods as in Example 1-1. Table 3 shows the results of XPS measurement of the bead surfaces and XPS measurement of the entire beads, by the same methods as in Example 1-1.

Comparative Example 1-10

Beads for blood processing were prepared in the same manner as Example 1-1, except that the beads selected were PuroSorb™ PAD950 instead of AMBERLITE™ XAD™ 1180N, the composition of the coating polymer was MEA/DEAEMA/CMB=80/10/10 (molar ratio), and the coating amount of the coating polymer was 20 mg/g dry beads. Elemental analysis by the same method as in Example 1-1 showed the nitrogen element ratio to be ≤0.3 weight %. Table 2 shows the results of evaluating the platelet adhesion by the same method as in Example 1-1.

Comparative Example 1-11

Beads for blood processing were prepared in the same manner as Comparative Example 1-2, except that the beads selected were PuroSorb™ PAD950 instead of AMBERLITE™ XAD™ 1180N, and the coating amount of the coating polymer was 63 mg/g dry beads. Elemental analysis by the same method as in Example 1-1 showed the nitrogen element ratio to be ≤0.3 weight %. Table 2 shows the results of evaluating the platelet adhesion by the same method as in Example 1-1.

Comparative Example 1-12

Beads for blood processing were prepared in the same manner as Comparative Example 1-5, except that the beads selected were PuroSorb™ PAD950 instead of AMBERLITE™ XAD™ 1180N, and the coating amount of the coating polymer was 24 mg/g dry beads. Elemental analysis by the same method as in Example 1-1 showed the nitrogen element ratio to be ≤0.3 weight %. Table 2 shows the results of evaluating the platelet adhesion by the same method as in Example 1-1.

Comparative Example 1-13

Beads for blood processing were prepared in the same manner as Comparative Example 1-6, except that the beads selected were PuroSorb™ PAD950 instead of AMBERLITE™ XAD™ 1180N, and the coating amount of the coating polymer was 114 mg/g dry beads. Elemental analysis by the same method as in Example 1-1 showed the nitrogen element ratio to be ≤0.3 weight %. Table 2 shows the results of evaluating the cytokine adsorption performance and platelet adhesion, by the same methods as in Example 1-1.

Comparative Example 1-14

Beads for blood processing were prepared in the same manner as Comparative Example 1-7, except that the beads selected were PuroSorb™ PAD950 instead of AMBERLITE™ XAD™ 1180N, and the coating amount of the coating polymer was 23 mg/g dry beads. Elemental analysis by the same method as in Example 1-1 showed the nitrogen element ratio to be ≤0.3 weight %. Table 2 shows the results of evaluating the cytokine adsorption performance and platelet adhesion, by the same methods as in Example 1-1.

Comparative Example 1-15

Beads for blood processing were prepared in the same manner as Comparative Example 1-8, except that the beads selected were PuroSorb™ PAD950 instead of AMBERLITE™ XAD™ 1180N, and the coating amount of the coating polymer was 70 mg/g dry beads. Elemental analysis by the same method as in Example 1-1 showed the nitrogen element ratio to be ≤0.3 weight %. Table 2 shows the results of evaluating the cytokine adsorption performance and platelet adhesion, by the same methods as in Example 1-1.

Comparative Example 1-16

Beads for blood processing were prepared in the same manner as Comparative Example 1-9, except that the beads selected were PuroSorb™ PAD950 instead of AMBERLITE™ XAD™ 1180N, and the coating amount of the coating polymer was 107 mg/g dry beads. Elemental analysis by the same method as in Example 1-1 showed the nitrogen element ratio to be ≤0.3 weight %. Table 2 shows the results of evaluating the cytokine adsorption performance and platelet adhesion, by the same methods as in Example 1-1. Table 3 shows the results of XPS measurement of the bead surfaces and XPS measurement of the entire beads, by the same methods as in Example 1-1.

Comparative Example 1-17

Beads for blood processing were prepared in the same manner as Example 1-1, except that the coating polymer used was PVP (polyvinylpyrrolidone K90, product of FujiFilm-Wako Pure Chemical Industries, Ltd.), the coating polymer concentration of the coating solution used was 0.5 wt %, and the coating amount of the coating polymer was 35 mg/g dry beads. Elemental analysis by the same method as in Example 1-1 showed the nitrogen element ratio to be ≤0.3 weight %. Table 1 shows the results of evaluating the platelet adhesion by the same method as in Example 1-1.

Comparative Example 1-18

Beads for blood processing were prepared in the same manner as Example 1-1, except that the coating polymer concentration of the coating solution used was 0 wt %, and the coating amount of the coating polymer was 0 mg/g dry beads. Elemental analysis by the same method as in Example 1-1 showed the nitrogen element ratio to be ≤0.3 weight %. Table 1 shows the results of evaluating the cytokine adsorption performance and platelet adhesion, by the same methods as in Example 1-1. Table 3 shows the results of XPS measurement of the bead surfaces and XPS measurement of the entire beads, by the same methods as in Example 1-1.

Comparative Example 1-19

Beads for blood processing were prepared in the same manner as Comparative Example 1-17, except that the beads selected were PuroSorb™ PAD950 instead of AMBERLITE™ XAD™ 1180N, and the coating amount of the coating polymer was 34 mg/g dry beads. Elemental analysis by the same method as in Example 1-1 showed the nitrogen element ratio to be ≤0.3 weight %. Table 2 shows the results of evaluating the platelet adhesion by the same method as in Example 1-1.

Comparative Example 1-20

Beads for blood processing were prepared in the same manner as Comparative Example 1-18, except that the beads selected were PuroSorb™ PAD950 instead of AMBERLITE™ XAD™ 1180N. Elemental analysis by the same method as in Example 1-1 showed the nitrogen element ratio to be ≤0.3 weight %. Table 2 shows the results of evaluating the cytokine adsorption performance and platelet adhesion, by the same methods as in Example 1-1. Table 3 shows the results of XPS measurement of the bead surfaces and XPS measurement of the entire beads, by the same methods as in Example 1-1.

Tables 1 and 2 below show the compositions of the biocompatible polymers (coating agents), the types of porous beads, the supported amounts (coated amounts) of the biocompatible polymers, the biocompatibility (platelet adhesion) of the beads for blood processing and the cytokine adsorption of the beads for blood processing, for the Examples and Comparative Examples of the first embodiment. Table 3 shows the atomic ratios based on XPS measurement of the surfaces and entireties of the beads for blood processing, for the Examples and Comparative Examples.

The nitrogen element ratios based on elemental analysis of the beads for blood processing used in the Examples and Comparative Examples according to the first embodiment were 0.3 weight % or lower in all of the beads for blood processing. The sums of the carbon, hydrogen and oxygen element ratios based on elemental analysis of the beads for blood processing were 99.0 weight % or higher for all of the beads for blood processing.

TABLE 1

| | Beads | Coating agent | Coating amount (mg) | Coating Polymer concentration | Platelet adhesion rate (%) | IL-1b adsorption rate (%) | IL-6 adsorption rate (%) | IL-8 adsorption rate (%) | IL-10 adsorption rate (%) | TNF-a adsorption rate (%) | HMGB1 adsorption rate (%) |
|---|---|---|---|---|---|---|---|---|---|---|---|
| Example 1-1 | XAD1180N | MEMA/DEAEMA/CMB = 80/10/10 | 6 | 0.1 wt % | 9 | 87 | 71 | 97 | 73 | 63 | 47 |
| Example 1-2 | XAD1180N | MEMA/DEAEMA/CMB = 60/20/20 | 6 | 0.1 wt % | 10 | | | | | | |
| Example 1-3 | XAD1180N | MEMA/CMB = 75/25 | 8 | 0.1 wt % | 6 | 87 | 70 | 97 | 73 | 62 | 50 |
| Example 1-4 | XAD1180N | MEMA/CMB = 75/25 | 31 | 0.5 wt % | 3 | 83 | 66 | 93 | 72 | 63 | 49 |
| Example 1-5 | XAD1180N | MEMA/CMB = 75/25 | 2.4 | 0.033 wt % | 7 | 89 | 72 | 98 | 74 | 65 | 55 |
| Example 1-6 | XAD1180N | MEMA/DEAEMA = 80/20 | 10 | 0.1 wt % | 7 | | | | | | |
| Example 1-7 | XAD1180N | MEMA/DEAEMA/AAc = 60/28/12 | 8 | 0.1 wt % | 6 | | | | | | |
| Example 1-8 | XAD1180N | MEMA/DEAEMA/AAc = 71/15/14 | 5 | 0.1 wt % | 6 | 87 | 71 | 97 | 73 | 65 | 49 |
| Example 1-9 | XAD1180N | MEMA/DEAEMA/MAc = 62/15/23 | 4 | 0.1 wt % | 6 | 88 | 72 | 98 | 73 | 66 | 44 |
| Example 1-10 | XAD1180N | MEMA = 100 | 11 | 0.1 wt % | 14 | 83 | 65 | 97 | 55 | 59 | 46 |
| Example 1-11 | XAD1180N | BMA/DEAEMA/CMB = 80/10/10 | 4 | 0.1 wt % | 8 | | | | | | |
| Example 1-12 | XAD1180N | BMA/CMB = 70/30 | 6 | 0.1 wt % | 8 | | | | | | |
| Example 1-13 | XAD1180N | LMA/DEAEMA/CMB = 80/10/10 | 4 | 0.1 wt % | 11 | | | | | | |
| Example 1-14 | XAD1180N | LMA/DEAEMA/CMB = 60/20/20 | 4 | 0.1 wt % | 11 | | | | | | |
| Example 1-15 | XAD1180N | LMA/DEAEMA/CMB = 40/30/30 | 6 | 0.1 wt % | 8 | | | | | | |
| Example 1-16 | XAD1180N | LMA/CMB = 70/30 | 5 | 0.1 wt % | 11 | | | | | | |
| Example 1-17 | XAD1180N | MEMA/CMB = 85/15 | 9 | 0.1 wt % | 8 | | | | | | |
| Example 1-18 | XAD1180N | MEMA/MPC = 85/15 | 7 | 0.1 wt % | 9 | | | | | | |
| Example 1-19 | XAD1180N | MEMA/DMAEMA = 80/20 | 9 | 0.1 wt % | 8 | | | | | | |
| Comp. Ex. 1-1 | XAD1180N | MEA/DEAEMA/CMB = 80/10/10 | 55 | 0.3 wt % | 19 | 64 | 58 | 74 | 52 | 55 | 30 |
| Comp. Ex. 1-2 | XAD1180N | MEA/DEAEMA/CMB = 80/10/10 | 94 | 0.5 wt % | 15 | 50 | 52 | 60 | 44 | 47 | 26 |
| Comp. Ex. 1-3 | XAD1180N | BA = 100 | 16 | 0.1 wt % | 17 | | | | | | |
| Comp. Ex. 1-4 | XAD1180N | BA/DEAEMA/CMB = 60/20/20 | 12 | 0.1 wt % | 15 | | | | | | |

TABLE 1-continued

| | Beads | Coating agent | Coating amount (mg) | Coating Polymer concentration | Platelet adhesion rate (%) | IL-1b adsorption rate (%) | IL-6 adsorption rate (%) | IL-8 adsorption rate (%) | IL-10 adsorption rate (%) | TNF-a adsorption rate (%) | HMGB1 adsorption rate (%) |
|---|---|---|---|---|---|---|---|---|---|---|---|
| Comp. Ex. 1-5 | XAD1180N | MC3A = 100 | 19 | 0.1 wt % | 16 | | | | | | |
| Comp. Ex. 1-6 | XAD1180N | MC3A = 100 | 91 | 0.5 wt % | 5 | 54 | 54 | 66 | 49 | 60 | 22 |
| Comp. Ex. 1-7 | XAD1180N | MEA = 100 | 21 | 0.1 wt % | 22 | 83 | 70 | 94 | 70 | 71 | 48 |
| Comp. Ex. 1-8 | XAD1180N | MEA = 100 | 56 | 0.3 wt % | 12 | 68 | 61 | 81 | 58 | 67 | 32 |
| Comp. Ex. 1-9 | XAD1180N | MEA = 100 | 97 | 0.5 wt % | 8 | 55 | 56 | 69 | 51 | 65 | 30 |
| Comp. Ex. 1-17 | XAD1180N | PVP | 35 | 0.5 wt % | 31 | | | | | | |
| Comp. Ex. 1-18 | XAD1180N | — | 0 | 0.0 wt % | 27 | 90 | 76 | 98 | 75 | 71 | 51 |

TABLE 2

| | Beads | Coating agent | Coating amount (mg) | Coating Polymer concentration | Platelet adhesion rate (%) | IL-1b adsorption rate (%) | IL-6 adsorption rate (%) | IL-8 adsorption rate (%) | IL-10 adsorption rate (%) | TNF-a adsorption rate (%) | HMGB1 adsorption rate (%) |
|---|---|---|---|---|---|---|---|---|---|---|---|
| Example 1-20 | PAD950 | MEMA/DEAEMA/CMB = 80/10/10 | 14 | 0.1 wt % | 3 | | | | | | |
| Example 1-21 | PAD950 | MEMA/DEAEMA/CMB = 60/20/20 | 13 | 0.1 wt % | 6 | | | | | | |
| Example 1-22 | PAD950 | MEMA/CMB = 75/25 | 6 | 0.1 wt % | 5 | 44 | 70 | 88 | 76 | 66 | 42 |
| Example 1-23 | PAD950 | MEMA/CMB = 75/25 | 19 | 0.5 wt % | 1 | 41 | 67 | 94 | 73 | 60 | 38 |
| Example 1-24 | PAD950 | MEMA/DEAEMA = 80/20 | 16 | 0.1 wt % | 8 | | | | | | |
| Example 1-25 | PAD950 | MEMA/DEAEMA/AAc = 60/28/12 | 13 | 0.1 wt % | 5 | | | | | | |
| Example 1-26 | PAD950 | MEMA = 100 | 15 | 0.1 wt % | 5 | | | | | | |
| Comp. Ex. 1-10 | PAD950 | MEA/DEAEMA/CMB = 80/10/10 | 20 | 0.1 wt % | 11 | | | | | | |
| Comp. Ex. 1-11 | PAD950 | MEA/DEAEMA/CMB = 80/10/10 | 63 | 0.5 wt % | 10 | | | | | | |
| Comp. Ex. 1-12 | PAD950 | MC3A = 100 | 24 | 0.1 wt % | 11 | | | | | | |
| Comp. Ex. 1-13 | PAD950 | MC3A = 100 | 114 | 0.5 wt % | 10 | 22 | 57 | 62 | 55 | 52 | 24 |
| Comp. Ex. 1-14 | PAD950 | MEA = 100 | 23 | 0.1 wt % | 10 | 41 | 68 | 83 | 73 | 62 | 36 |
| Comp. Ex. 1-15 | PAD950 | MEA = 100 | 70 | 0.3 wt % | 10 | 33 | 63 | 77 | 65 | 62 | 35 |
| Comp. Ex. 1-16 | PAD950 | MEA = 100 | 107 | 0.5 wt % | 10 | 25 | 59 | 65 | 58 | 60 | 27 |
| Comp. Ex. 1-19 | PAD950 | PVP | 34 | 0.5 wt % | 16 | | | | | | |
| Comp. Ex. 1-20 | PAD950 | — | 0 | 0.0 wt % | 13 | 46 | 74 | 92 | 78 | 67 | 45 |

TABLE 3

| | | | Atomic abundance ratio with respect to total atoms with atomic numbers of 3-92, on bead surfaces | | | Atomic abundance ratio with respect to total atoms with atomic numbers of 3-92, in entirety of beads | | |
|---|---|---|---|---|---|---|---|---|
| | Beads | Coating agent | Carbon + oxygen | Nitrogen | Phosphorus | Carbon + oxygen | Nitrogen | Phosphorus |
| Example 1-1 | XAD1180N | MEMA/DEAEMA/CMB = 80/10/10 | 99.6% | 0.4% | ≤0.1% | ≥99.8% | ≤0.1% | ≤0.1% |
| Example 1-3 | XAD1180N | MEMA/CMB = 75/25 | 99.5% | 0.5% | ≤0.1% | | | |

TABLE 3-continued

| | Beads | Coating agent | Atomic abundance ratio with respect to total atoms with atomic numbers of 3-92, on bead surfaces | | | Atomic abundance ratio with respect to total atoms with atomic numbers of 3-92, in entirety of beads | | |
|---|---|---|---|---|---|---|---|---|
| | | | Carbon + oxygen | Nitrogen | Phosphorus | Carbon + oxygen | Nitrogen | Phosphorus |
| Example 1-4 | XAD1180N | MEMA/CMB = 75/25 | 99.3% | 0.7% | ≤0.1% | | | |
| Example 1-5 | XAD1180N | MEMA/CMB = 75/25 | 99.8% | 0.2% | ≤0.1% | | | |
| Example 1-6 | XAD1180N | MEMA/DEAEMA = 80/20 | 99.5% | 0.5% | ≤0.1% | | | |
| Example 1-8 | XAD1180N | MEMA/DEAEMA/AAc = 71/15/14 | 99.8% | 0.2% | ≤0.1% | | | |
| Example 1-12 | XAD1180N | BMA/CMB = 70/30 | 99.5% | 0.5% | ≤0.1% | | | |
| Example 1-15 | XAD1180N | LMA/DEAEMA/CMB = 40/30/30 | 99.4% | 0.6% | ≤0.1% | | | |
| Example 1-18 | XAD1180N | MEMA/MPC = 85/15 | 99.4% | 0.3% | ≤0.1% | | | |
| Comp. Ex. 1-1 | XAD1180N | MEA/DEAEMA/CMB = 80/10/10 | 99.1% | 0.9% | 0.3% | | | |
| Comp. Ex. 1-7 | XAD1180N | MEA = 100 | ≥99.8% | ≤0.1% | ≤0.1% | | | |
| Comp. Ex. 1-9 | XAD1180N | MEA = 100 | ≥99.8% | ≤0.1% | ≤0.1% | | | |
| Comp. Ex. 1-18 | XAD1180N | — | ≥99.8% | ≤0.1% | ≤0.1% | | | |
| Example 1-20 | PAD950 | MEMA/DEAEMA/CMB = 80/10/10 | 99.6% | 0.4% | ≤0.1% | | | |
| Example 1-22 | PAD950 | MEMA/CMB = 75/25 | 99.6% | 0.4% | ≤0.1% | | | |
| Comp. Ex. 1-16 | PAD950 | MEA = 100 | ≥99.8% | ≤0.1% | ≤0.1% | | | |
| Comp. Ex. 1-20 | PAD950 | — | ≥99.8% | ≤0.1% | ≤0.1% | | | |

[Chemical Formula 9]

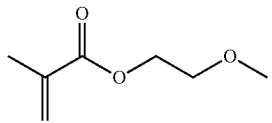 (i)

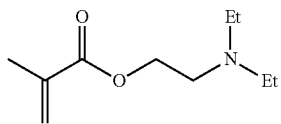 (ii)

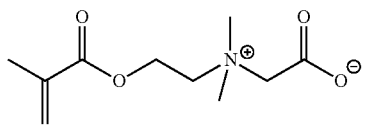 (iii)

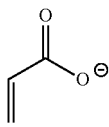 (iv)

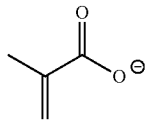 (v)

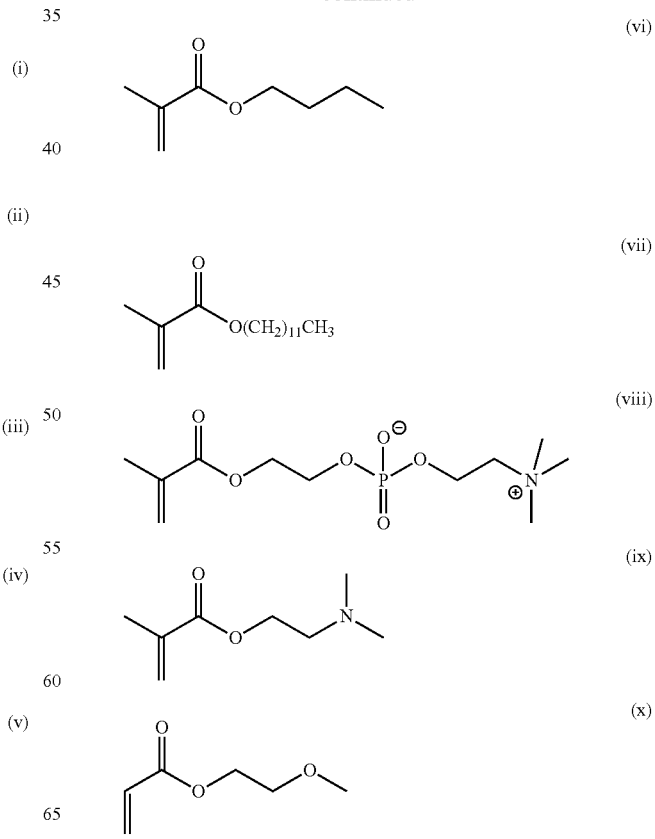

-continued

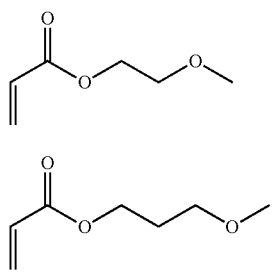

(xi)

(xii)

Referring to Tables 1 and 2, the beads for blood processing of the Examples had lower supported amounts of biocompatible polymer than the beads for blood processing of the Comparative Examples, with greater blood compatibility while maintaining high adsorption of the porous beads.

The biocompatible polymers of Examples 1-1 to 1-19 in Table 1 all had platelet adhesion rates of 14% or lower even with coating amounts of 11 mg and lower. In contrast, the biocompatible polymers of Comparative Examples 1-1 to 1-5, 1-7 and 1-18 had platelet adhesion rates of 15% or higher with coating amounts of 21 mg or lower. When the coating amount was 50 mg or higher as in Comparative Examples 1-6, 1-8 and 1-9, the platelet adhesion rate was 14% or lower, but the cytokine adsorption was markedly reduced. Similarly, the polymers of Examples 1-20 to 1-26 in Table 2 all had platelet adhesion rates of 8% or lower even with coating amounts of 20 mg and lower. In contrast, the polymers of Comparative Examples 1-10 to 1-16 and 1-20 all had platelet adhesion rates of 10% or higher even with coating amounts of 20 mg or higher.

Referring to Tables 1 to 3, with the beads for blood processing of Examples 1-1, 1-3 to 1-6, 1-8, 1-12, 1-15, 1-18, 1-20 and 1-22, the ratios of nitrogen atoms on the surfaces of the beads for blood processing were 0.2% to 0.7% as the percentage of atoms based on the total number of atoms with atomic numbers of 3 to 92, thus showing that the supported amount of biocompatible polymer was smaller, the adsorption of the porous beads was higher and the blood compatibility was improved, compared to the beads for blood processing of the Comparative Examples.

2. Examples and Comparative Examples for Second Embodiment

Example 2-1

<Synthesis of Coating Polymer>

A copolymer of 2-methoxyethyl methacrylate (MEMA, compound of structural formula (i) in [Chemical Formula 10]), N,N-diethylaminoethyl methacrylate (DEAEMA, compound of structural formula (ii) in [Chemical Formula 10]) and N-methacryloyloxyethyl-N,N-dimethylammonium-α-N-methylcarboxybetaine (CMB, compound of structural formula (iii) in [Chemical Formula 10]) was synthesized by common solution polymerization. The polymerization conditions were a concentration of 1 mol/L for each monomer, in an ethanol solution in the presence of 0.0025 mol/L of azoisobutyronitrile (AIBN) as an initiator, and polymerization reaction was conducted for 8 hours at a reaction temperature of 60° C., to obtain a polymer solution. The obtained polymer solution was dropped into diethyl ether and the precipitated polymer was recovered. The recovered polymer was purified by a reprecipitation procedure using diethyl ether. The obtained polymer was then dried for 24 hours under reduced pressure conditions to obtain a coating polymer.

The molar ratio of the MEMA monomer unit, the DEAEMA monomer unit and the CMB monomer unit in the coating polymer was measured in the following manner. The obtained coating polymer was dissolved in dimethyl sulfoxide, and then calculation was performed by the following formula from the peak at 4.32 ppm (from H atoms unique to CMB) and the peak at 2.63 ppm (from H atoms unique to DEAEMA), in a chart calculated after carrying out $^1$H-NMR measurement, and the area ratio at 0.65 to 2.15 ppm (total H atoms).

DEAEMA monomer molar ratio=("Area ratio in 2.63 ppm range"/2)/("area ratio in 0.65 to 2.15 ppm range"/5−"area ratio in 2.63 ppm range"×0.3)×100

CMB monomer molar ratio=("Area ratio in 4.32 ppm range"/2)/("area ratio in 0.65 to 2.15 ppm range"/5−"area ratio in 2.63 ppm range"×0.3)×100

MEMA monomer molar ratio=100−DEAEMA monomer molar ratio−CMB monomer molar ratio

The molar ratio of the MEMA monomer unit, the DEAEMA monomer unit and the CMB monomer unit for the coating polymer was calculated to be 80/10/10.

<Preparation of Coating Solution>

After adding the coating polymer to 57 W/W % ethyl alcohol, the mixture was stirred for 12 hours to prepare a coating solution with a coating polymer concentration of 0.2 wt %.

<Preparation of Beads>

The porous beads used were AMBERLITE™ XAD™ 1180N (product of Organo Co., Ltd., styrene-based polymer beads, volume-average particle size: 609 μm, cumulative pore capacity of 1.472 cm$^3$/g for pore sizes of 5 nm to 100 nm, cumulative pore capacity of 0.020 cm$^3$/g for pore sizes of 100 nm to 200 nm). A graph of the log differential pore volume distribution and cumulative pore capacity of AMBERLITE™ XAD™ 1180N is shown in FIG. 1, and a graph of the cumulative volume particle size distribution is shown in FIG. 3. After placing 8 mL of ultrapure water-swelled beads (1.76 g dry weight) in a 50 mL polypropylene (PP) conical tube, 40 mL of 57 W/W % ethyl alcohol was added. A shaker (InVitro Shaker WAVE-S1, product of Taitec Co.) was used for 12 hours of shaking at 40 r/min at a shaking angle of 10 degrees, and then the shaken solution was filtered with a cell strainer (Cell Strainer, 70 μm nylon mesh, product of Funakoshi Corp.). After measuring the absorbance of the filtered solution at 220 nm using a Shimadzu UV-2600 Ultraviolet/visible spectrophotometer (product of Shimadzu Corp.), the filtered beads were again added to a 50 mL conical tube. The procedure including addition of 57 W/W % ethyl alcohol to the conical tube, shaking for 12 hours with the shaker and solution removal with the cell strainer was repeated until the absorbance of the filtered solution at 220 nm reached 0.03 or lower.

<Preparation of Coated Beads>

After adding 40 mL of the coating solution to the 50 mL conical tube containing the treated beads, a shaker (InVitro Shaker WAVE-S1, product of Taitec Co.) was used for shaking at 40 r/min for 12 hours at a shaking angle of 10 degrees. The coated solution was then filtered with a cell strainer (Cell Strainer, 70 μm nylon mesh, product of Funakoshi Corp.) to obtain coated beads. After measuring the absorbance of the filtered coated solution at 220 nm using a Shimadzu UV-2600 Ultraviolet/visible spectrophotometer (product of Shimadzu Corp.), the filtered coated beads were again added to a 50 mL conical tube.

After then vacuum drying the 50 mL conical tube containing the coated beads for 15 hours at 50° C. (absolute pressure: ≤0.003 MPa), 40 mL of 20 W/W % ethyl alcohol was added to the conical tube. A shaker (InVitro Shaker WAVE-S1, product of Taitec) was used for shaking at 40 r/min for 12 hours at a shaking angle of 10 degrees, and then the solution in which the beads were swelled was removed with a cell strainer (Cell Strainer, 70 μm nylon mesh, product of Funakoshi Corp.), and the resulting beads were again added to a 50 mL conical tube. The procedure of addition of 40 mL of ultrapure water to the 50 mL conical tube, shaking for 3 hours with the shaker and solution removal with the cell strainer was then repeated a total of 3 times, to obtain coated beads. The amount of elution of the obtained coated beads was measured to be ≤1.0 mg, which was a low amount of elution.

<Preparation of Beads for Blood Processing>

A 3 mL portion of the coated beads was added to a 15 mL conical tube. The procedure of addition of 12 mL of ultrapure water to the 15 mL conical tube, shaking for 3 hours with the shaker and solution removal with the cell strainer was then repeated a total of 2 times. Finally, the conical tube was filled with 12 mL of physiological saline (Otsuka Normal Saline, product of Otsuka Pharmaceutical Factory, Inc.), and sterilization was carried out with γ-ray irradiation to obtain beads for blood processing.

<Measurement of Physical Properties of Beads for Blood Processing>

<Overall Elemental Analysis of Beads for Blood Processing>

The solution in 1 mL of the beads for blood processing was removed with a cell strainer, and the resulting beads were added to a 15 mL conical tube. Next, 12 mL of ultrapure water was added to the 15 mL conical tube to replace the bead solution with ultrapure water. The beads for blood processing replaced with ultrapure water were vacuum dried for 15 hours at 50° C. (absolute pressure: ≤0.003 MPa). The dried beads for blood processing were subjected to elemental analysis using an elemental analyzer (EMGA-930 oxygen/nitrogen/hydrogen analyzer by Horiba, Ltd.). The analysis was conducted with 3 samples, and the average value was recorded. The nitrogen element ratio was found to be ≤0.3 weight %.

<XPS Measurement of Surfaces of Beads for Blood Processing>

After randomly selecting 50 of the dried beads for blood processing, the surface condition of each bead was measured by XPS using a K-Alpha+ (product of Thermo Fisher Scientific). The measuring conditions were: Irradiated x-rays: single crystal spectroscopy Al Kα, X-ray spot diameter: 150 μm, neutralizing electron gun: used. The averaged value for the abundance ratio of nitrogen atoms with respect to the total number of lithium atoms (atomic number: 3) to uranium atoms (atomic number: 92) on the surfaces of the 50 beads for blood processing was calculated as the abundance ratio (%) of nitrogen atoms on the surfaces of the beads for blood processing. The results are shown in Table 6.

<XPS Measurement of Entirety of Beads for Blood Processing>

The dried beads for blood processing were ground with a pestle to prepare powder of the beads for blood processing. The surface condition of the powder was measured by XPS using a K-Alpha+ (product of Thermo Fisher Scientific). The measuring conditions were: Irradiated x-rays: single crystal spectroscopy Al Kα, X-ray spot diameter: 150 μm, neutralizing electron gun: used. The measurement was conducted for 10 samples, and the averaged value for the abundance ratio of nitrogen atoms with respect to the total number of lithium atoms (atomic number: 3) to uranium atoms (atomic number: 92) was calculated as the abundance ratio (%) of nitrogen atoms for the entirety of the beads for blood processing. The results are shown in Table 6.

<Platelet Adhesion of Beads for Blood Processing by Flow Evaluation Method>

Figure 4:
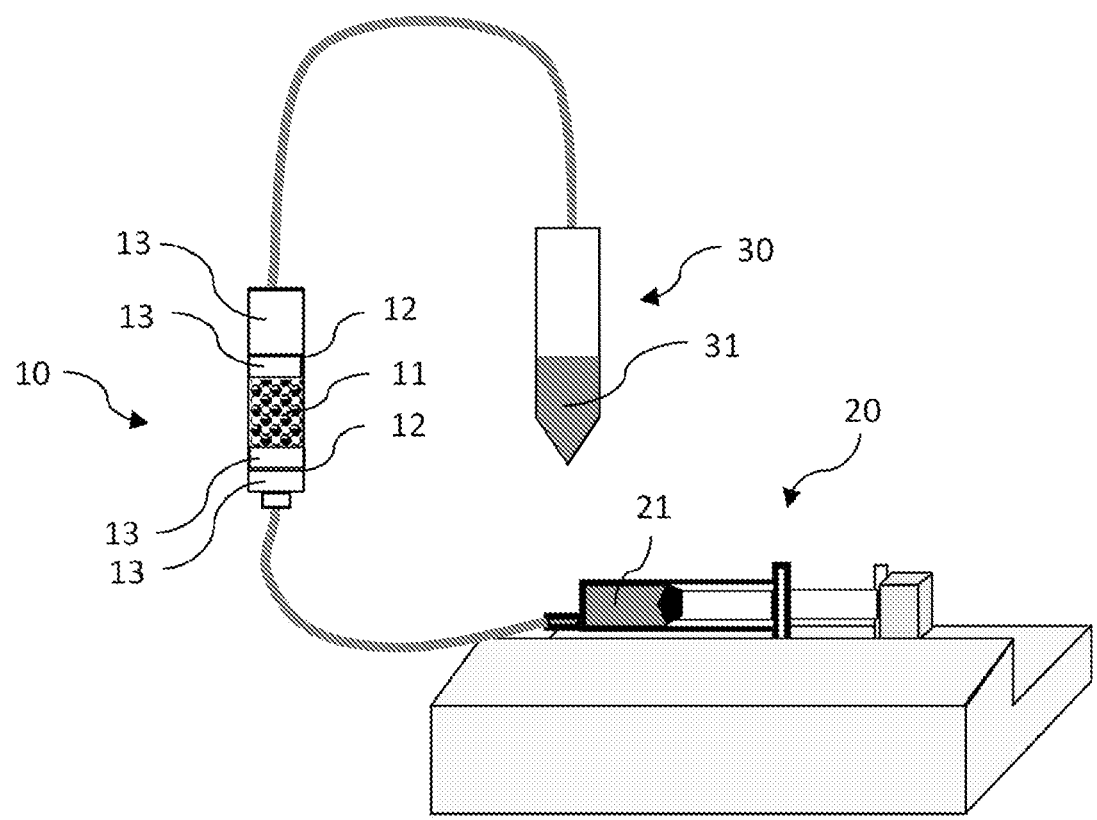
FIG. 4 is a schematic diagram illustrating a method for evaluating platelet adhesion.

FIG. 4 is a schematic diagram illustrating a method for evaluating platelet adhesion. A 1.5 mL portion of beads for blood processing (0.33 g dry weight) was swelled with physiological saline (Otsuka Normal Saline, product of Otsuka Pharmaceutical Factory, Inc.). The swelled beads for blood processing (11) were packed into a 2.5 mL syringe, taking care to avoid infiltration of air. The beads for blood processing were sandwiched above and below by a mesh (12) and O-ring(13), as shown in FIG. 4, to avoid leakage of the beads. A mini-column (10) packed with 1.5 mL of the beads for blood processing was prepared.

Heparin sodium (heparin sodium injection, 50,000 unit/50 mL, product of Nipro Corp.) was added to blood collected from a healthy volunteer, to a concentration of 1000 IU/mL (this will be referred to as "untreated blood (21)"). Next, an experiment circuit was assembled as shown in FIG. 4, circulating physiological saline (Otsuka Normal Saline, product of Otsuka Pharmaceutical Factory, Inc.) through the mini-column (10) packed with the beads for blood processing, for 10 minutes at a flow rate of 1 mL/min, using a syringe pump (20) (TE-351, product of Terumo Corp.). The untreated blood (21) was then circulated at a flow rate of 1 mL/min using a syringe pump (20) (TE-351, product of Terumo Corp.). Two minutes after starting circulation of the untreated blood, the blood circulated through the mini-column was sampled in a 15 mL conical tube (30), stopping circulation of the blood when the amount of sampled blood (this will be referred to as "treated blood (31)") reached 9 mL. The platelet concentrations of the treated blood and untreated blood were measured using an XT-1800i Micro cell counter (product of Sysmex), and the platelet residue rate on the beads was calculated by the following formula to be 85%. The platelet adhesion on the beads for blood processing was judged to be high when the platelet residue rate determined by this method was 80% or lower, and the platelet adhesion on the beads for blood processing was judged to be low when the platelet residue rate was higher than 80%.

Platelet residue rate (%)=(Platelet count of treated blood/(platelet count of untreated blood)×100

The untreated blood used for this experiment had a leukocyte concentration of 5310/μL, an erythrocyte concentration of 505×10$^4$/μL, a platelet concentration of 196×10$^3$/L and a hematocrit of 41.0%. The activation clotting time of the untreated blood was 319 seconds, as measured with a Hemochron Jr. Signature+ (product of International Technidyne Corp., JACT-LR Hemochron test cartridge).

Example 2-2

Coated beads and beads for blood processing similar to Example 2-1 were prepared, except that the composition of the coating polymer was MEMA/CMB=90/10 (molar ratio). The amount of elution of the obtained coated beads was measured by the same method as Example 2-1 to be ≤1.0 mg, which was a low amount of elution. Elemental analysis of the beads for blood processing by the same method as Example 2-1 showed a nitrogen element ratio of 0.3 weight %. When the platelet adhesion was evaluated by the same method as Example 2-1, the platelet residue rate was 83% and the platelet adhesion was low. Table 6 shows the results of XPS measurement of the bead surfaces and XPS measurement of the entire beads, by the same methods as in Example 2-1.

<Adsorption of Beads for Blood Processing>

Heparin sodium (heparin sodium injection, 50,000 unit/50 mL, product of Nipro Corp.) was added to blood collected from a healthy volunteer, to a concentration of 2000 IU/mL, and then *Escherichia coli* O111:B4-derived lipopolysaccharide (LPS) (product of Sigma-Aldrich) was added to a concentration of 0.1 µg/mL and a shaker (InVitro Shaker WAVE-S1, product of Taitec) was used for shaking at 10 r/min for 24 hours at 37° C., with a shaking angle of 10 degrees. A centrifuge (6200 Hybrid high-speed refrigerated centrifuge, product of Kubota Corp.) was then used for centrifugation at 2000 g for 20 minutes at room temperature, and the supernatant was obtained as the blood plasma sample. After mixing 3.6 mL of the obtained blood plasma sample and 0.45 mL of the beads for blood processing (0.10 g dry weight) in a 5 mL polypropylene (PP) tube, a shaker was used for shaking at 10 r/min for 2 hours at 37° C., with a shaking angle of 10 degrees (for use as a bead-contact sample). A sample was also prepared without addition of beads to 3.6 mL of the obtained blood plasma sample, and was treated in the same manner as the bead-contact sample (for use as the non-bead-contact sample). The shaken PP tube was centrifuged at 2000 g for 1 minute at room temperature using a centrifuge, to obtain supernatants of the bead-contact and non-bead-contact samples. The supernatants were used for measurement of different cytokine concentrations using a Bio-Plex system (product of Bio-Rad, Bio-Plex Pro human cytokine G27-plex panel), according to the manufacturer's instruction manual. The HMGB-1 concentration was measured using an HMGB1 ELISAK Kit II (product of Shino-Test Corp.), according to the manufacturer's instruction manual. The cytokine and HMGB-1 adsorption rates of the beads were calculated by the following formulas. The results are shown in Table 5.

Cytokine adsorption rate (%)=("Cytokine concentration of non-bead-contact sample"–"cytokine concentration of bead-contact sample")/"cytokine concentration of non-bead-contact sample"×100

HMGB-1 adsorption rate (%)=("HMGB-1 concentration of non-bead-contact sample"–"HMGB-1 concentration of bead-contact sample")/ "HMGB-1 concentration of non-bead-contact sample"×100

The cytokine concentrations for the non-bead-contact sample and the HMGB-1 concentration for the non-bead-contact sample for this experiment were IL-1b: 3658 pg/mL, IL-6: 5540 pg/mL, IL-8: 6144 pg/mL, IL-10: 846 pg/mL, TNF-α: 8085 pg/mL and HMGB-1: 27 ng/mL.

Example 2-3

Coated beads and beads for blood processing similar to Example 2-1 were prepared, except that the composition of the coating polymer was MEMA/CMB=80/20 (molar ratio). The elution of the obtained coated beads was measured by the same method as Example 2-1 to be ≤1.0 mg, which was a low amount of elution. Elemental analysis of the beads for blood processing by the same method as Example 2-1 showed a nitrogen element ratio of 0.3 weight %. When the platelet adhesion was evaluated by the same method as Example 2-1, the platelet residue rate was 89% and the platelet adhesion was low. Table 6 shows the results of XPS measurement of the bead surfaces and XPS measurement of the entire beads, by the same methods as in Example 2-1. Table 5 shows the results of evaluating the cytokine adsorption performance and platelet adhesion, by the same methods as in Example 2-2.

Example 2-4

Coated beads and beads for blood processing similar to Example 2-1 were prepared, except that the composition of the coating polymer was MEMA/CMB=70/30 (molar ratio). The elution of the obtained coated beads was measured by the same method as Example 2-1 to be ≤1.0 mg, which was a low amount of elution. Elemental analysis of the beads for blood processing by the same method as Example 2-1 showed a nitrogen element ratio of 0.3 weight %. When the platelet adhesion was evaluated by the same method as Example 2-1, the platelet residue rate was 89% and the platelet adhesion was low.

Example 2-5

Coated beads and beads for blood processing similar to Example 2-1 were prepared, except that the composition of the coating polymer was MEMA/MPC (2-(methacryloyloxy)ethyl 2-(trimethylammonio)ethyl phosphate, compound of structural formula (iv) in [Chemical Formula 10])=85/15 (molar ratio). The elution of the obtained coated beads was measured by the same method as Example 2-1 to be ≤1.0 mg, which was a low amount of elution. Elemental analysis of the beads for blood processing by the same method as Example 2-1 showed a nitrogen element ratio of 0.3 weight %. When the platelet adhesion was evaluated by the same method as Example 2-1, the platelet residue rate was 83% and the platelet adhesion was low. Table 6 shows the results of XPS measurement of the bead surfaces and XPS measurement of the entire beads, by the same methods as in Example 2-1.

Example 2-6

Coated beads and beads for blood processing similar to Example 2-1 were prepared, except that the composition of the coating polymer was MEMA/SPB (2-(methacryloyloxy)ethyl]dimethyl-(3-sulfopropyl)ammonium hydroxide, compound of structural formula (v) in [Chemical Formula 10])= 88/12 (molar ratio). The elution of the obtained coated beads was measured by the same method as Example 2-1 to be ≤1.0 mg, which was a low amount of elution. Elemental analysis of the beads for blood processing by the same method as Example 2-1 showed a nitrogen element ratio of ≤0.3 weight %. When the platelet adhesion was evaluated by the same method as Example 2-1, the platelet residue rate was 84% and the platelet adhesion was low. Table 6 shows the results of XPS measurement of the bead surfaces and XPS measurement of the entire beads, by the same methods as in Example 2-1.

Example 2-7

Coated beads and beads for blood processing similar to Example 2-1 were prepared, except that the composition of the coating polymer was MEMA/SPB=70/30 (molar ratio).

The elution of the obtained coated beads was measured by the same method as Example 2-1 to be ≤1.0 mg, which was a low amount of elution. Elemental analysis of the beads for blood processing by the same method as Example 2-1 showed a nitrogen element ratio of ≤0.3 weight %. When the platelet adhesion was evaluated by the same method as Example 2-1, the platelet residue rate was 87% and the platelet adhesion was low.

Example 2-8

Coated beads and beads for blood processing similar to Example 2-1 were prepared, except that the composition of the coating polymer was MEMA/SPBA ([3-(methacryloylamino)propyl]dimethyl(3-sulfopropyl)ammonium hydroxide, compound of structural formula (vi) in [Chemical Formula 10])=88/12 (molar ratio). The elution of the obtained coated beads was measured by the same method as Example 2-1 to be ≤1.0 mg, which was a low amount of elution. Elemental analysis of the beads for blood processing by the same method as Example 2-1 showed a nitrogen element ratio of 0.3 weight %. When the platelet adhesion was evaluated by the same method as Example 2-1, the platelet residue rate was 83% and the platelet adhesion was low.

Example 2-9

Coated beads and beads for blood processing similar to Example 2-1 were prepared, except that the composition of the coating polymer was MEA (2-methoxyethyl acrylate, compound of structural formula (vii) in [Chemical Formula 10])/CMB=70/30 (molar ratio). The elution of the obtained coated beads was measured by the same method as Example 2-1 to be ≤1.0 mg, which was a low amount of elution. Elemental analysis of the beads for blood processing by the same method as Example 2-1 showed a nitrogen element ratio of ≤0.3 weight %. When the platelet adhesion was evaluated by the same method as Example 2-1, the platelet residue rate was 85% and the platelet adhesion was low. Table 6 shows the results of XPS measurement of the bead surfaces and XPS measurement of the entire beads, by the same methods as in Example 2-1. Table 5 shows the results of evaluating the cytokine adsorption performance and platelet adhesion, by the same methods as in Example 2-2.

Example 2-10

Coated beads and beads for blood processing similar to Example 2-1 were prepared, except that the composition of the coating polymer was MC3A (3-methoxypropyl acrylate, compound of structural formula (viii) in [Chemical Formula 10])/CMB=70/30 (molar ratio). The elution of the obtained coated beads was measured by the same method as Example 2-1 to be 1.0 mg, which was a low amount of elution. Elemental analysis of the beads for blood processing by the same method as Example 2-1 showed a nitrogen element ratio of 0.3 weight %. When the platelet adhesion was evaluated by the same method as Example 2-1, the platelet residue rate was 87% and the platelet adhesion was low.

Example 2-11

Coated beads and beads for blood processing similar to Example 2-1 were prepared, except that the composition of the coating polymer was Et2A (2-(2-ethoxyethoxy)ethyl acrylate, compound of structural formula (ix) in [Chemical Formula 10])/CMB=70/30 (molar ratio). The elution of the obtained coated beads was measured by the same method as Example 2-1 to be ≤1.0 mg, which was a low amount of elution. Elemental analysis of the beads for blood processing by the same method as Example 2-1 showed a nitrogen element ratio of 0.3 weight %. When the platelet adhesion was evaluated by the same method as Example 2-1, the platelet residue rate was 86% and the platelet adhesion was low.

Example 2-12

Coated beads and beads for blood processing similar to Example 2-1 were prepared, except that the beads selected were PuroSorb™ PAD950 (product of Purolite Corp., acrylic polymer beads, volume-average particle size: 621 μm, cumulative pore capacity for pore sizes of 5 nm to 100 nm: 0.823 cm$^3$/g, cumulative pore capacity for pore sizes of 100 nm to 200 nm: 0.038 cm$^3$/g) instead of AMBERLITE™ XAD™ 1180N. A graph of the log differential pore volume distribution and cumulative pore capacity of PuroSorb™ PAD950 is shown in FIG. 2, and a graph of the cumulative volume particle size distribution is shown in FIG. 3. The elution of the obtained coated beads was measured by the same method as Example 2-1 to be ≤1.0 mg, which was a low amount of elution. Elemental analysis of the beads for blood processing by the same method as Example 2-1 showed a nitrogen element ratio of 0.3 weight %. When the platelet adhesion was evaluated by the same method as Example 2-1, the platelet residue rate was 91% and the platelet adhesion was low. Table 6 shows the results of XPS measurement of the bead surfaces and XPS measurement of the entire beads, by the same methods as in Example 2-1.

Example 2-13

Coated beads and beads for blood processing similar to Example 2-1 were prepared, except that the beads selected were PuroSorb™ PAD950 instead of AMBERLITE™ XAD™ 1180N, and the composition of the coating polymer was MEMA/DEAEMA/CMB=60/20/20 (molar ratio). The elution of the obtained coated beads was measured by the same method as Example 2-1 to be ≤1.0 mg, which was a low amount of elution. Elemental analysis of the beads for blood processing by the same method as Example 2-1 showed a nitrogen element ratio of 0.3 weight %. When the platelet adhesion was evaluated by the same method as Example 2-1, the platelet residue rate was 86% and the platelet adhesion was low.

Example 2-14

Coated beads and beads for blood processing similar to Example 2-3 were prepared, except that the beads selected were PuroSorb™ PAD950 instead of AMBERLITE™ XAD™ 1180N. The elution of the obtained coated beads was measured by the same method as Example 2-1 to be ≤1.0 mg, which was a low amount of elution. Elemental analysis of the beads for blood processing by the same method as Example 2-1 showed a nitrogen element ratio of 0.3 weight %. When the platelet adhesion was evaluated by the same method as Example 2-1, the platelet residue rate was 87% and the platelet adhesion was low. Table 6 shows the results of XPS measurement of the bead surfaces and XPS measurement of the entire beads, by the same methods as in Example 2-1.

Example 2-15

Coated beads and beads for blood processing similar to Example 2-7 were prepared, except that the beads selected were PuroSorb™ PAD950 instead of AMBERLITE™ XAD™ 1180N. The elution of the obtained coated beads was measured by the same method as Example 2-1 to be ≤1.0 mg, which was a low amount of elution. Elemental analysis of the beads for blood processing by the same method as Example 2-1 showed a nitrogen element ratio of 0.3 weight %. When the platelet adhesion was evaluated by the same method as Example 2-1, the platelet residue rate was 85% and the platelet adhesion was low.

Example 2-16

Coated beads and beads for blood processing similar to Example 2-9 were prepared, except that the beads selected were PuroSorb™ PAD950 instead of AMBERLITE™ XAD™ 1180N. The elution of the obtained coated beads was measured by the same method as Example 2-1 to be ≤1.0 mg, which was a low amount of elution. Elemental analysis of the beads for blood processing by the same method as Example 2-1 showed a nitrogen element ratio of 0.3 weight %. When the platelet adhesion was evaluated by the same method as Example 2-1, the platelet residue rate was 85% and the platelet adhesion was low. Table 6 shows the results of XPS measurement of the bead surfaces and XPS measurement of the entire beads, by the same methods as in Example 2-1. Table 5 shows the results of evaluating the cytokine adsorption performance and platelet adhesion, by the same methods as in Example 2-2.

Example 2-17

Coated beads and beads for blood processing similar to Example 2-10 were prepared, except that the beads selected were PuroSorb™ PAD950 instead of AMBERLITE™ XAD™ 1180N. The elution of the obtained coated beads was measured by the same method as Example 2-1 to be ≤1.0 mg, which was a low amount of elution. Elemental analysis of the beads for blood processing by the same method as Example 2-1 showed a nitrogen element ratio of 0.3 weight %. When the platelet adhesion was evaluated by the same method as Example 2-1, the platelet residue rate was 88% and the platelet adhesion was low.

Comparative Example 2-1

Coated beads and beads for blood processing similar to Example 2-1 were prepared, except that the coating polymer concentration of the coating solution used was 0 wt % (the coating polymer was not dissolved). The elution of the obtained coated beads was measured by the same method as Example 2-1 to be ≤1.0 mg, which was a low amount of elution. Elemental analysis of the beads for blood processing by the same method as Example 2-1 showed a nitrogen element ratio of 0.3 weight %. When the platelet adhesion was evaluated by the same method as Example 2-1, the platelet residue rate was 74% and the platelet adhesion was high. Table 6 shows the results of XPS measurement of the bead surfaces and XPS measurement of the entire beads, by the same methods as in Example 2-1. Table 5 shows the results of evaluating the cytokine adsorption performance and platelet adhesion, by the same methods as in Example 2-2.

Comparative Example 2-2

Coated beads and beads for blood processing similar to Example 2-1 were prepared, except that the composition of the coating polymer was MEMA=100 (molar ratio). The elution of the obtained coated beads was measured by the same method as Example 2-1 to be ≤1.0 mg, which was a low amount of elution. Elemental analysis of the beads for blood processing by the same method as Example 2-1 showed a nitrogen element ratio of 0.3 weight %. When the platelet adhesion was evaluated by the same method as Example 2-1, the platelet residue rate was 79% and the platelet adhesion was high. Table 6 shows the results of XPS measurement of the bead surfaces and XPS measurement of the entire beads, by the same methods as in Example 2-1. Table 5 shows the results of evaluating the cytokine adsorption performance and platelet adhesion, by the same methods as in Example 2-2.

Comparative Example 2-3

Coated beads and beads for blood processing similar to Example 2-1 were prepared, except that the composition of the coating polymer was MEMA/CMB=95/5 (molar ratio). The elution of the obtained coated beads was measured by the same method as Example 2-1 to be ≤1.0 mg, which was a low amount of elution. Elemental analysis of the beads for blood processing by the same method as Example 2-1 showed a nitrogen element ratio of 0.3 weight %. When the platelet adhesion was evaluated by the same method as Example 2-1, the platelet residue rate was 79% and the platelet adhesion was high. Table 6 shows the results of XPS measurement of the bead surfaces and XPS measurement of the entire beads, by the same methods as in Example 2-1.

Comparative Example 2-4

Coated beads and beads for blood processing similar to Example 2-1 were prepared, except that the composition of the coating polymer was MEMA/CMB=60/40 (molar ratio). The elution of the obtained coated beads was measured by the same method as Example 2-1 to be 1.2 mg, which was a high amount of elution. Elemental analysis of the beads for blood processing by the same method as Example 2-1 showed a nitrogen element ratio of 0.3 weight %.

Comparative Example 2-5

Coated beads and beads for blood processing similar to Example 2-1 were prepared, except that the composition of the coating polymer was MEA/DEAEMA/CMB=40/20/40 (molar ratio). Coated beads and beads for blood processing similar to Example 2-1 were prepared. The elution of the obtained coated beads was measured by the same method as Example 2-1 to be 1.4 mg, which was a high amount of elution. Elemental analysis of the beads for blood processing by the same method as Example 2-1 showed a nitrogen element ratio of 0.3 weight %. Table 6 shows the results of XPS measurement of the bead surfaces and XPS measurement of the entire beads, by the same methods as in Example 2-1.

Comparative Example 2-6

Coated beads and beads for blood processing similar to Comparative Example 2-1 were prepared, except that the beads selected were PuroSorb™ PAD950 instead of AMBERLITE™ XAD™ 1180N. The elution of the obtained coated beads was measured by the same method as Example 2-1 to be ≤1.0 mg, which was a low amount of elution. Elemental analysis of the beads for blood processing by the same method as Example 2-1 showed a nitrogen element ratio of 0.3 weight %. When the platelet adhesion was evaluated by the same method as Example 2-1, the platelet residue rate was 80% and the platelet adhesion was high. Table 6 shows the results of XPS measurement of the bead surfaces and XPS measurement of the entire beads, by the same methods as in Example 2-1. Table 5 shows the results of evaluating the cytokine adsorption performance and platelet adhesion, by the same methods as in Example 2-2.

Comparative Example 2-7

Coated beads and beads for blood processing similar to Comparative Example 2-5 were prepared, except that the beads selected were PuroSorb™ PAD950 instead of AMBERLITE™ XAD™ 1180N. The elution of the obtained coated beads was measured by the same method as Example 2-1 to be 1.4 mg, which was a high amount of elution. Elemental analysis of the beads for blood processing by the same method as Example 2-1 showed a nitrogen element ratio of 0.3 weight %. Table 6 shows the results of XPS measurement of the bead surfaces and XPS measurement of the entire beads, by the same methods as in Example 2-1.

Comparative Example 2-8

(Synthesis of Beads)

A uniform mixture comprising 100 g of vinyl acetate, 64.3 g of triallyl isocyanurate, 100 g of ethyl acetate, 100 g of heptane, 7.5 g of polyvinyl acetate (polymerization degree: 500), 3.8 g of azoisobutyronitrile (AIBN), and 400 mL of ultrapure water dissolving 1 wt % of polyvinyl alcohol (saponification degree: 87-89%), 0.05 wt % of sodium dihydrogenphosphate dihydrate and 1.5 wt % of disodium hydrogenphosphate dodecahydrate, were placed in a flask and heated for 18 hours at 65° C. and for 5 hours at 75° C., while stirring thoroughly, for suspension polymerization. The particulate copolymer obtained by filtering the solution was rinsed with ultrapure water, and then rinsed by acetone extraction. Finally, the rinsed particulate copolymer was stirred for 18 hours at 40° C. in a solution comprising 46.5 g of caustic soda and 2 L of methanol, to obtain PVA polymer beads (volume-average particle size: 110 μm, cumulative pore capacity of 0.270 cm$^3$/g for pore sizes of 5 nm to 100 nm, cumulative pore capacity of ≤0.005 cm$^3$/g for pore sizes of 100 nm to 200 nm).

Coated beads similar to Comparative Example 2-1 were prepared, except that the beads selected were the obtained PVA polymer beads instead of AMBERLITE™ XAD™ 1180N. Elution of the beads determined by the same method as Example 2-1 was assessed to be low, with an elution amount of ≤1.0 mg.

Comparative Example 2-9

Coated beads similar to Comparative Example 2-1 were used, except that the beads selected were the obtained PVA polymer beads instead of AMBERLITE™ XAD™ 1180N. Elution of the beads determined by the same method as Example 2-1 was assessed to be high, with an elution amount of 1.8 mg.

Comparative Example 2-10

Coated beads similar to Comparative Example 2-3 were used, except that the beads selected were the obtained PVA polymer beads instead of AMBERLITE™ XAD™ 1180N. Elution of the beads determined by the same method as Example 2-1 was assessed to be high, with an elution amount of 2.0 mg.

Comparative Example 2-11

Coated beads similar to Comparative Example 2-4 were used, except that the beads selected were the obtained PVA polymer beads instead of AMBERLITE™ XAD™ 1180N. Elution of the beads determined by the same method as Example 2-1 was assessed to be high, with an elution amount of 2.3 mg.

Comparative Example 2-12

Coated beads similar to Comparative Example 2-6 were used, except that the beads selected were the obtained PVA polymer beads instead of AMBERLITE™ XAD™ 1180N. Elution of the beads determined by the same method as Example 2-1 was assessed to be high, with an elution amount of 1.9 mg.

Comparative Example 2-13

Coated beads similar to Comparative Example 2-7 were used, except that the beads selected were the obtained PVA polymer beads instead of AMBERLITE™ XAD™ 1180N. Elution of the beads determined by the same method as Example 2-1 was assessed to be high, with an elution amount of 2.2 mg.

Comparative Example 2-14

Coated beads similar to Comparative Example 2-8 were used, except that the beads selected were the obtained PVA polymer beads instead of AMBERLITE™ XAD™ 1180N. Elution of the beads determined by the same method as Example 2-1 was assessed to be high, with an elution amount of 2.1 mg.

Comparative Example 2-15

Coated beads similar to Comparative Example 2-9 were used, except that the beads selected were the obtained PVA polymer beads instead of AMBERLITE™ XAD™ 1180N. Elution of the beads determined by the same method as Example 2-1 was assessed to be high, with an elution amount of 1.3 mg.

Comparative Example 2-16

Coated beads similar to Comparative Example 2-10 were used, except that the beads selected were the obtained PVA polymer beads instead of AMBERLITE™ XAD™ 1180N. Elution of the beads determined by the same method as Example 2-1 was assessed to be high, with an elution amount of 1.2 mg.

Comparative Example 2-17

Coated beads similar to Comparative Example 2-1 were prepared, except that the beads selected were active carbon beads (product of Kureha Corp., mean particle size: 576 μm, cumulative pore capacity for pore sizes of 5 nm to 100 nm: 0.134 cm$^3$/g, cumulative pore capacity for pore sizes of 100 nm to 200 nm: 0.005 cm$^3$/g), instead of AMBERLITE™

XAD™ 1180N. The elution of the obtained coated beads was measured by the same method as Example 2-1 to be ≤1.0 mg, which was a low amount of elution.

Comparative Example 2-18

Coated beads similar to Example 2-4 were prepared, except that the beads selected were active carbon beads (product of Kureha Corp., mean particle size: 576 μm, cumulative pore capacity for pore sizes of 5 nm to 100 nm: 0.134 cm$^3$/g, cumulative pore capacity for pore sizes of 100 nm to 200 nm: 0.005 cm$^3$/g), instead of AMBERLITE™ XAD™ 1180N. The elution of the obtained coated beads was measured by the same method as Example 2-1 to be 1.2 mg, which was a high amount of elution.

Tables 4 and 5 below show the compositions of the biocompatible polymers (coating agents), the types of porous beads, the measurement results for elution of the coated beads and the biocompatibility (platelet adhesion) of the beads for blood processing, for the Examples and Comparative Examples of the second embodiment. Table 6 shows the atomic ratios based on XPS measurement of the surfaces and entireties of the beads for blood processing, for the Examples and Comparative Examples.

The nitrogen element ratios based on elemental analysis of the beads for blood processing used in the Examples and Comparative Examples according to the second embodiment were 0.3 weight % or lower in all of the beads for blood processing. The sums of the carbon, hydrogen and oxygen element ratios based on elemental analysis of the beads for blood processing were 99.0 weight % or higher for all of the beads for blood processing.

TABLE 4

| Example | Beads | Polymer | Elution of polymer of coated beads | Platelet adhesion of beads for blood processing |
|---|---|---|---|---|
| Example 2-1 | Styrene beads | MEMA/DEAEMA/CMB = 80/10/10 | ≤1.0 mg | Low |
| Example 2-2 | | MEMA/CMB = 90/10 | ≤1.0 mg | |
| Example 2-3 | | MEMA/CMB = 80/20 | ≤1.0 mg | |
| Example 2-4 | | MEMA/CMB = 70/30 | ≤1.0 mg | |
| Example 2-5 | | MEMA/MPC = 85/15 | ≤1.0 mg | |
| Example 2-6 | | MEMA/SPB = 88/12 | ≤1.0 mg | |
| Example 2-7 | | MEMA/SPB = 70/30 | ≤1.0 mg | |
| Example 2-8 | | MEMA/SPBA = 88/12 | ≤1.0 mg | |
| Example 2-9 | | MEA/CMB = 70/30 | ≤1.0 mg | |
| Example 2-10 | | MC3A/CMB = 70/30 | ≤1.0 mg | |
| Example 2-11 | | Et2A/CMB = 70/30 | ≤1.0 mg | |
| Comp. Ex. 2-1 | | — | ≤1.0 mg | High |
| Comp. Ex. 2-2 | | MEMA = 100 | ≤1.0 mg | |
| Comp. Ex. 2-3 | | MEMA/CMB = 95/5 | ≤1.0 mg | |
| Comp. Ex. 2-4 | | MEMA/CMB = 60/40 | 1.2 mg | |
| Comp. Ex. 2-5 | | MEA/DEAEMA/CMB = 40/20/40 | 1.4 mg | |
| Example 2-12 | Acryl beads | MEMA/DEAEMA/CMB = 80/10/10 | ≤1.0 mg | Low |
| Example 2-13 | | MEMA/DEAEMA/CMB = 60/20/20 | ≤1.0 mg | |
| Example 2-14 | | MEMA/CMB = 80/20 | ≤1.0 mg | |
| Example 2-15 | | MEMA/SPB = 70/30 | ≤1.0 mg | |
| Example 2-16 | | MEA/CMB = 70/30 | ≤1.0 mg | |
| Example 2-17 | | MC3A/CMB = 70/30 | ≤1.0 mg | |
| Comp. Ex. 2-6 | | — | ≤1.0 mg | High |
| Comp. Ex. 2-7 | | MEA/DEAEMA/CMB = 40/20/40 | 1.4 mg | |
| Comp. Ex. 2-8 | PVA beads | Not coated | ≤1.0 mg | |
| Comp. Ex. 2-9 | | MEMA/DEAEMA/CMB = 80/10/10 | 1.8 mg | |
| Comp. Ex. 2-10 | | MEMA/CMB = 80/20 | 2.0 mg | |
| Comp. Ex. 2-11 | | MEMA/CMB = 70/30 | 2.3 mg | |
| Comp. Ex. 2-12 | | MEMA/SPB = 88/12 | 1.9 mg | |
| Comp. Ex. 2-13 | | MEMA/SPB = 70/30 | 2.2 mg | |
| Comp. Ex. 2-14 | | MEMA/SPBA = 88/12 | 2.1 mg | |
| Comp. Ex. 2-15 | | MEA/CMB = 70/30 | 1.3 mg | |
| Comp. Ex. 2-16 | | MC3A/CMB = 70/30 | 1.2 mg | |
| Comp. Ex. 2-17 | Active carbon beads | Not coated | ≤1.0 mg | |
| Comp. Ex. 2-18 | | MEMA/CMB = 70/30 | 1.2 mg | |

TABLE 5

| Example | Beads | Polymer | IL-1b Adsorption rate (%) | IL-6 Adsorption rate (%) | IL-8 Adsorption rate (%) | IL-10 Adsorption rate (%) | TNF-a Adsorption rate (%) | HMGB1 Adsorption rate (%) |
|---|---|---|---|---|---|---|---|---|
| Examle 2-2 | Styrene beads | MEMA/CMB = 90/10 | 83 | 66 | 96 | 61 | 62 | 47 |
| Examle 2-3 | | MEMA/CMB = 80/20 | 84 | 67 | 96 | 65 | 65 | 44 |
| Examle 2-9 | | MEA/CMB = 70/30 | 75 | 62 | 82 | 60 | 58 | 39 |
| Comp. Ex. 2-1 | | Not coated | 90 | 76 | 98 | 75 | 71 | 51 |
| Comp. Ex. 2-2 | | MEMA = 100 | 80 | 62 | 95 | 48 | 53 | 44 |
| Example 2-16 | Acryl beads | MEA/CMB = 70/30 | 41 | 65 | 87 | 69 | 61 | 37 |
| Comp. Ex. 2-6 | | Not coated | 46 | 74 | 92 | 78 | 67 | 45 |

TABLE 6

| | Beads | Coating agent | Atomic abundance ratio with respect to total atoms with atomic numbers of 3-92, on bead surfaces | | | Atomic abundance ratio with respect to total atoms with atomic numbers of 3-92, in entirety of beads | | |
|---|---|---|---|---|---|---|---|---|
| | | | Carbon + oxygen | Nitrogen | Phosphorus | Carbon + oxygen | Nitrogen | Phosphorus |
| Example 2-1 | Styrene beads | MEMA/DEAEMA/CMB = 80/10/10 | 99.5% | 0.5% | ≤0.1% | ≥99.8% | ≤0.1% | ≤0.1% |
| Example 2-2 | | MEMA/CMB = 90/10 | 99.8% | 0.2% | ≤0.1% | | | |
| Example 2-3 | | MEMA/CMB = 80/20 | 99.5% | 0.5% | ≤0.1% | | | |
| Example 2-5 | | MEMA/MPC = 85/15 | 99.2% | 0.4% | 0.4% | | | |
| Example 2-6 | | MEMA/SPB = 88/12 | 99.8% | 0.2% | ≤0.1% | | | |
| Example 2-9 | | MEA/CMB = 70/30 | 99.2% | 0.8% | ≤0.1% | | | |
| Comp. Ex. 2-1 | | — | ≥99.8% | ≤0.1% | ≤0.1% | | | |
| Comp. Ex. 2-2 | | MEMA = 100 | ≥99.8% | ≤0.1% | ≤0.1% | | | |
| Comp. Ex. 2-3 | | MEMA/CMB = 95/5 | ≥99.8% | ≤0.1% | ≤0.1% | | | |
| Comp. Ex. 2-5 | | MEA/DEAEMA/CMB = 40/20/40 | 98.8% | 1.2% | ≤0.1% | | | |
| Example 2-12 | Acryl beads | MEMA/DEAEMA/CMB = 80/10/10 | 99.5% | 0.5% | ≤0.1% | | | |
| Example 2-14 | | MEMA/CMB = 80/20 | 99.5% | 0.5% | ≤0.1% | | | |
| Example 2-16 | | MEA/CMB = 70/30 | 99.1% | 0.9% | ≤0.1% | | | |
| Comp. Ex. 2-6 | | — | 99.8% | ≤0.1% | ≤0.1% | | | |
| Comp. Ex. 2-7 | | MEA/DEAEMA/CMB = 40/20/40 | 98.7% | 1.3% | ≤0.1% | | | |

[Chemical Formula 10]

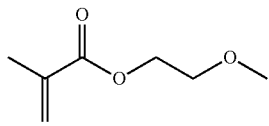

(i)

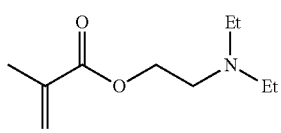

(ii)

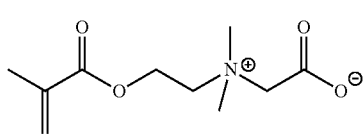

(iii)

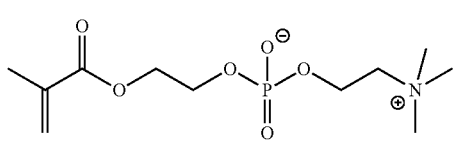

(iv)

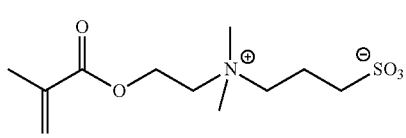

(v)

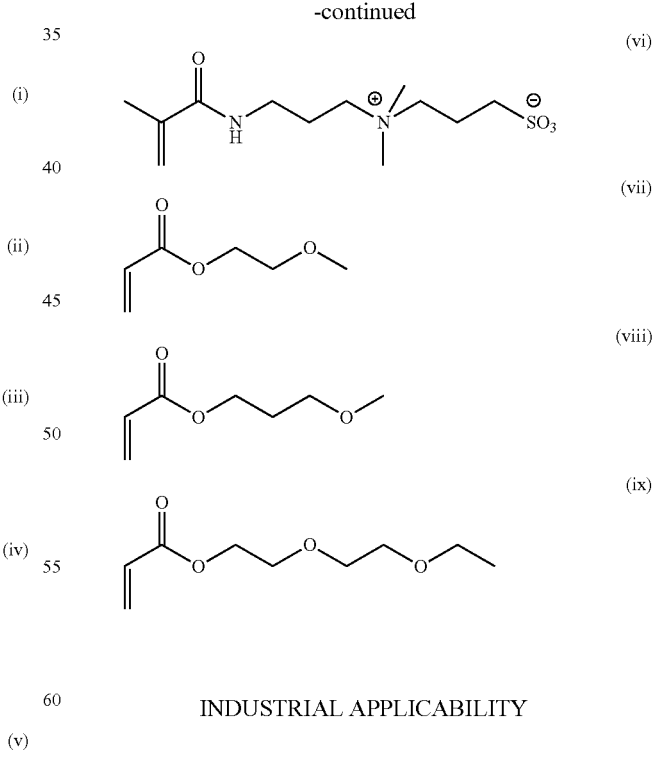

(vi), (vii), (viii), (ix)

INDUSTRIAL APPLICABILITY

The beads for blood processing of the invention can be used for treatment of ischemic disease including sepsis, for example. The beads for blood processing of the invention are expected to have application not only for treatment of ischemic disease but also for other situations in which excess production of inflammatory mediators is problematic, such as heart surgery and organ transplantation surgery.

REFERENCE SIGNS LIST

10 Mini-column
11 Beads for blood processing
12 Mesh
13 O-ring
20 Syringe pump
21 Untreated blood
30 Conical tube
31 Treated blood

The invention claimed is:

1. Beads for blood processing comprising porous beads and a polymer supported on the surfaces of the porous beads, wherein:
the porous beads are composed of at least one resin selected from the group consisting of acrylic-based resins, styrene-based resins and cellulose-based resins, and
the polymer includes, as a monomer unit, a monomer represented by following formula (1):

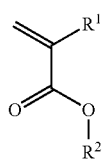 (1)

where $R^1$ is $-CH_3$, $R^2$ is $-CH_2(CH_2)_qOCH_3$ or $-CH_2C_mH_{2m+1}$, q is 1 to 5 and m is 0 to 17.

2. The beads for blood processing according to claim 1, wherein a proportion of nitrogen atoms on the surfaces of the beads for blood processing is 0.2% to 0.7%, as the percentage of atoms based on the total number of atoms with atomic numbers of 3 to 92.

3. The beads for blood processing according to claim 2, wherein the monomer represented by formula (1) is at least one selected from the group consisting of 2-methoxyethyl methacrylate, n-butyl methacrylate and lauryl methacrylate.

4. The beads for blood processing according to claim 1, wherein q is 1 or 2 and m is 0 to 11.

5. The beads for blood processing according to claim 4, wherein the content of the monomer represented by formula (1) is 40 mol % or greater with respect to the total monomers composing the polymer.

6. The beads for blood processing according to claim 5, wherein the polymer further includes an additional monomer with at least one group selected from the group consisting of amino, carboxyl, phosphate, sulfonate and zwitterionic groups.

7. The beads for blood processing according to claim 6, wherein the content of the additional monomer is 15 mol % to 40 mol % with respect to the total monomers composing the polymer.

8. The beads for blood processing according to claim 1, wherein the polymer further includes a charged monomer as a monomer unit.

9. The beads for blood processing according to claim 1, wherein the polymer further includes an additional monomer with at least one group selected from the group consisting of amino, carboxyl, phosphate, sulfonate and zwitterionic groups.

10. The beads for blood processing according to claim 9, wherein the additional monomer is at least one selected from the group consisting of 2-aminoethyl methacrylate (AEMA), dimethylaminoethyl methacrylate (DMAEMA), diethylaminoethyl methacrylate (DEAEMA), [2-(methacryloyloxy)ethyl]trimethylammonium, acrylic acid (AAc), methacrylic acid (MAc), N-methacryloyloxyethyl-N,N-dimethylammonium-α-N-methylcarboxybetaine (CMB) and 2-(methacryloyloxy)ethyl 2-(trimethylammonio)ethyl phosphate (MPC).

11. The beads for blood processing according to claim 1, wherein a proportion of the sum of carbon atoms and oxygen atoms on the surfaces of the beads for blood processing is 97.0% or higher, as the percentage of atoms based on the total number of atoms with atomic numbers of 3 to 92.

12. The beads for blood processing according to claim 1, wherein the amount of the polymer is 0.08 mg to 114 mg per 1 g of dry weight of the porous beads.

13. The beads for blood processing according to claim 1, wherein the amount of the polymer is 2.0 mg to 20 mg per 1 g of dry weight of the porous beads.

14. The beads for blood processing according to claim 1, wherein the porous beads have a volume-average particle size of 300 μm to 1000 μm.

15. The beads for blood processing according to claim 1, wherein the porous beads have a cumulative pore capacity for pore sizes of 5 nm to 100 nm of 0.5 cm³/g or higher and a cumulative pore capacity for pore sizes of 100 nm to 200 nm of 0.2 cm³/g or lower.

16. A blood purification device comprising the beads for blood processing according to claim 1.

17. The beads for blood processing according to claim 1, wherein the monomer represented by formula (1) is at least one selected from the group consisting of 2-methoxyethyl methacrylate, n-butyl methacrylate and lauryl methacrylate.

* * * * *